United States Patent [19]

Ts'o et al.

[11] Patent Number: 4,469,863
[45] Date of Patent: Sep. 4, 1984

[54] NONIONIC NUCLEIC ACID ALKYL AND ARYL PHOSPHONATES AND PROCESSES FOR MANUFACTURE AND USE THEREOF

[76] Inventors: Paul O. P. Ts'o, 2117 Folkstone Rd., Lutherville, Md. 21093; Paul S. Miller, 225 Hopkins Rd., Baltimore, Md. 21212

[21] Appl. No.: 206,297

[22] Filed: Nov. 12, 1980

[51] Int. Cl.³ .................... C07H 21/02; C07H 21/04; C07H 21/00
[52] U.S. Cl. ...................................... 536/27; 536/28; 536/29
[58] Field of Search .............................. 536/27, 28, 29

[56] References Cited

U.S. PATENT DOCUMENTS 3,560,478  2/1971  Myer .................................... 536/27

OTHER PUBLICATIONS

Agarwal, K., and Reftina, F., Nucleic Acids Research, vol. 6, pp. 3009–3024, 1979.
Miller, P., et al., Biochemistry, vol. 18, pp. 5134–5143, 1979, vol. 20, pp. 1874–1880, 1981.
Nemer, M. and Ogilvie, K., Tetrahedron Letters, vol. 21, pp. 4149–4152, 1980.
Miller, P., et al., Federation Proceedings, Abstract 2231, vol. 36, 1977.
Miller, P., et al., J. Am. Chem. Soc., vol. 93, pp. 6657–6665, 1971.
Pless, R., et al., Biochem., vol. 16, pp. 1239–1250, 1977.
Jayarama, K., et al., Proc. Natl. Acad. Sci., vol. 78, pp. 1537–1541, 1977.

Primary Examiner—Blondel Hazel
Attorney, Agent, or Firm—Walter G. Finch

[57] ABSTRACT

Oligonucleoside alkyl— or aryl phosphonates are nonionic analogues of nucleic acid which possess unique physical and biological properties. These properties enable the analogues to enter living cells intact and to bind with specifically selected nucleic acids within the cell. As a result, the analogues can specifically inhibit the function or expression of a preselected nucleic acid sequence. Thus the analogues could be used to specifically inhibit the growth of tumor cells or replication of viruses in infected cells.

Four methods are provided for preparing oligonucleoside methylphosphonates: (1) Coupling a protected nucleoside 3'-alkyl or aryl phosphonate with the 5'-hydroxyl group of a protected nucleoside using a condensing agent; (2) Coupling protected nucleoside 3'-alkyl or aryl phosphonic acid derivative with the 5'-hydroxy group of a protected nucleoside with the activated alkyl or aryl phosphonic acid derivative possessing functionalities which are good leaving groups; (3) Coupling a protected nucleoside 3'-alkyl or aryl phosphinate derivative with the 5'-hydroxyl group of a protected nucleoside with the resulting phosphinate derivative being then oxidized to the phosphonate; and (4) Converting a oligonucleoside methoxyphosphite derivative to the alkyl or aryl phosphonate derivative by reaction with an alkyl or aryl iodide. It has been demonstrated that procedures (1) and (2) can be used to prepare oligonucleoside methylphosphonates. Others have shown that procedure (4) can be used to prepare a diribonucleoside methylphosphonate.

7 Claims, 18 Drawing Figures

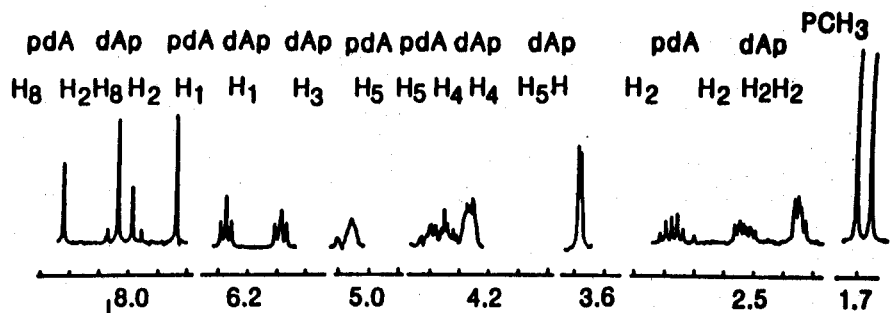
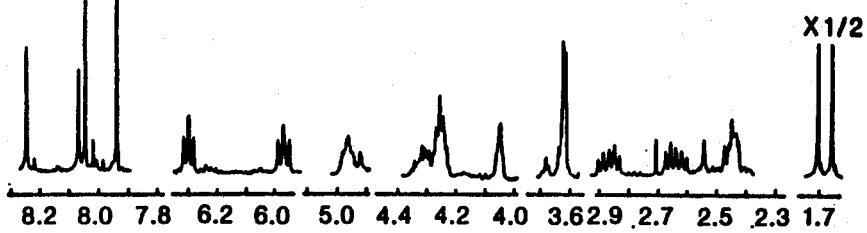
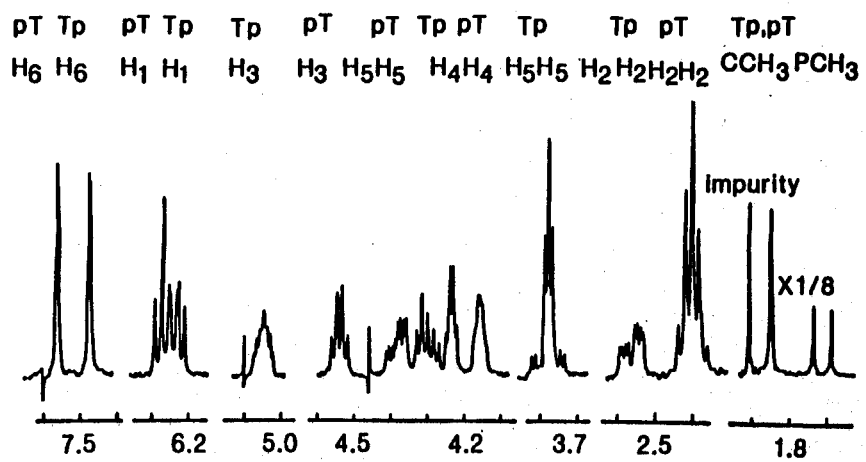
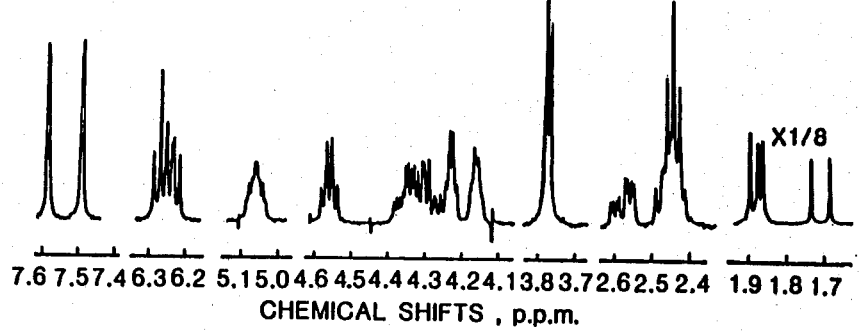
The 360-MHz $^1$H NMR spectra of (a) dApA$^1$, (b) dApA$^2$, (c) dTpT$^1$, and (d) dTpT$^2$ at 25 °C in D$_2$O containing 1 mM ethylenediaminetetracetate — 10 mM sodium phosphate, pH 7.0. The tentative chemical shift assignments appear above each dimer.

NONIONIC NUCLEIC ACID ALKYL AND ARYL PHOSPHONATES AND PROCESSES FOR MANUFACTURE AND USE THEREOF

This invention relates generally to biochemical and biological effects of nonionic nucleic acid methylphosphonates, and more particularly to nonionic nucleic acid alkyl and aryl methylphosphonates and processes for the manufacture and use thereof.

Prior to the present invention, studies on nucleic acid analogs and derivatives possessing modified internucleoside linkages have made important contributions to understanding nucleic acid conformation in solution and have provided materials for various biochemical and biological studies.

Recent studies have been made on the physical, biochemical and biological properties of one class of nonionic nucleic acid derivative, the oligonucleotide alkyl phosphotriesters.

The physical properties of dinucleotide methyl and ethyl phosphotriesters have been studied by ultraviolet, circular dichroism, infrared and proton nuclear magnetic resonance spectroscopy. The interaction of deoxyribooligonucleotide ethyl phosphotriesters with sequences complementary to the amino acid accepting stem and anticodon region of transfer RNA have been characterized and their inhibitory effects on in vitro aminoacylation have been studied. More recently, the inhibitory effect of a 2'-O-methylribooligonucleotide triester, $G_p{}^m(Et) G_p{}^m(Et)U$, on cellular protein synthesis and growth of mammalian cells in culture has been reported. In addition, selective binding of an octathymidylate ethyl phosphotriester, [Tp(Et)]$_7$T to polydeoxyadenylic acid has been extensively investigated.

An object of this invention is to provide nonionic nucleic acid alkyl or aryl phosphonates analogs.

Still another object of this invention is to teach the preparation of nonionic nucleic acid alkyl or aryl phosphonate analogs by several novel synthetic processes or methods.

To provide nonionic nucleic acid alkyl or aryl phosphonate analogs for interacting with complementary cellular or viral nucleic acids with the objective of controlling or regulating the function or expression of the cellular or viral nucleic acids, is still another object of this invention.

To provide a heptadeoxyribonucleoside methyl phosphonate with a base sequence which is complementary to the 3'-terminus of bacterial 16S ribosonal ribonucleic acid with objective of preventing bacterial protein synthesis, is a further object of this invention.

Even another object of this invention is to provide alkyl and aryl phosphonate nucleic acid analogs comprising at least two nucleosides, a base, and an alkyl or aryl phosphonate group, with the nucleosides being linked together to form alkyl or aryl phosphonate nucleic acid analogs for the purpose of controlling or regulating the function or expression of cellular or viral nucleic acids.

BRIEF DESCRIPTION OF THE DRAWINGS

FIG. 12 is spectral diagrams of the 360 MHz $^1$H nmr spectra of (a) d-ApA)$_1$; (b) d-ApA)$_2$; (c) d-TpT)$_1$; and (d) d-TpT)$_2$ at 25° C. in D$_2$O containing 1 mM ethylenediaminetetracetate-10 mM sodium phosphate, pH 7.0, with the tentative chemical shift assignments appear above each dimer;

DESCRIPTION OF THE PREFERRED EMBODIMENTS

Figure 2:
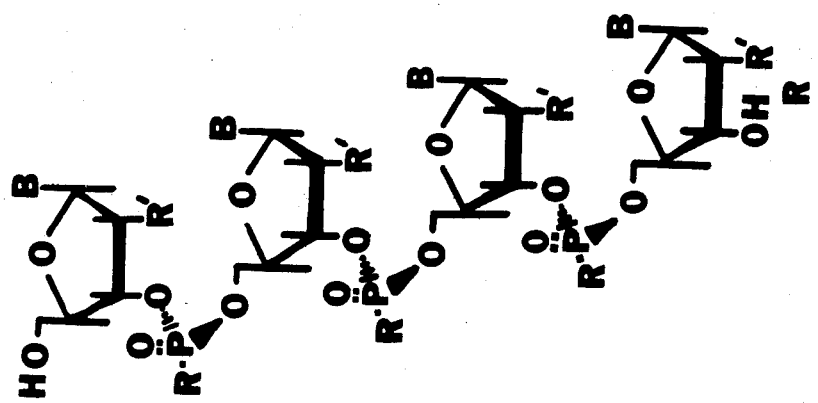
FIG. 2 illustrates the general molecular structure of an oligonucleoside alkyl or aryl phosphonate.
Figure 1:
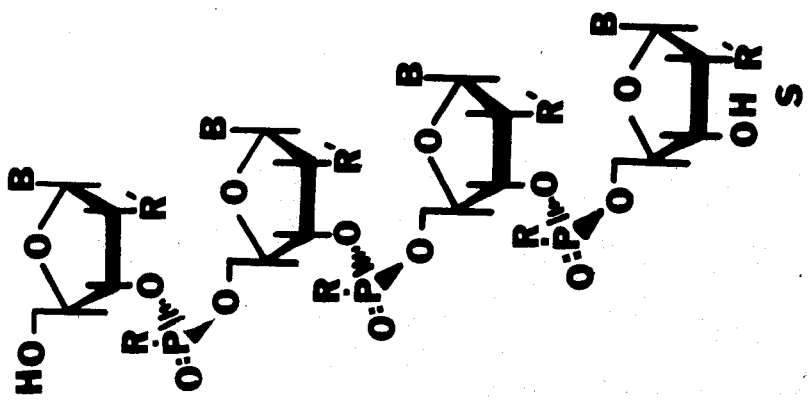
FIG. 1 shows the general molecular structure of an oligonucleoside alkyl or aryl phosphonate.

The general structure of the oligonucleoside alkyl or aryl phosphonates are shown in FIGS. 1 and 2.

FIG. 1 shows the general structure of an oligonucleoside alkyl or aryl phosphonate. The nucleoside units which consists of a base (B) comprising adenine, thymine, guanine, cytosine, uracil or hypoxanthine and a sugar where R' can be hydrogen, hydroxyl, O-alkyl or O-aryl or O-halogeno are linked in a 3'-5' manner by a phosphosphonate group where R can be alkyl or aryl. The configuration of the alkyl or aryl phosphonate group is S.

FIG. 2 shows the general structure of an oligonucleoside alkyl or aryl phosphonate. The nucleoside units which consists of a base (B) comprising adenine, thymine, guanine, cytosine, uracil or hypoxanthine and a sugar where R' can be hydrogen, hydroxyl, O-alkyl or O-aryl or O-halogeno are linked in a 3'→5' manner by a phosphosphonate group where R can be alkyl or aryl. The configuration of the alkyl or aryl phosphonate group is R.

Figure 3:
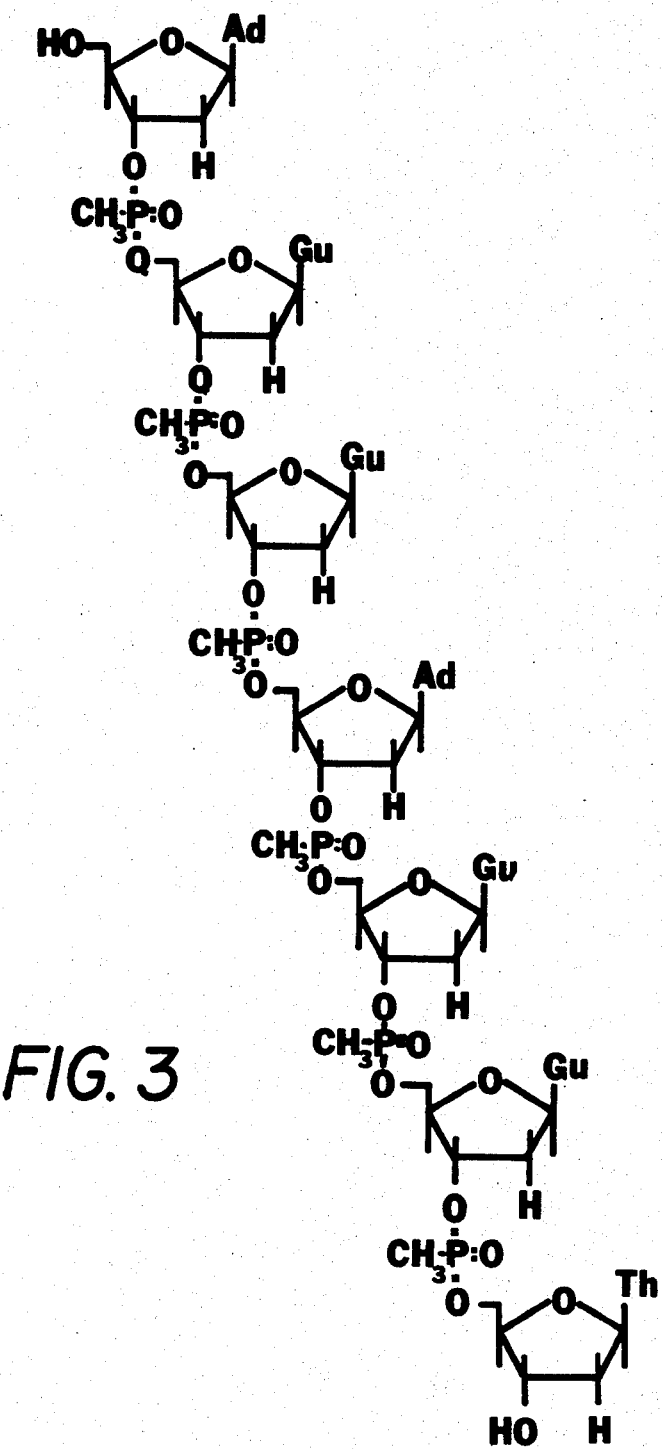
FIG. 3 illustrates the molecular structure of a heptadeoxyribonucleoside methylphosphonate.

A specific example of an oligodeoxyribonucleoside methylphosphonate is shown in FIG. 3.

In FIG. 3, there is shown the structure of a heptadeoxyribonucleoside methylphosphonate. The deoxyribonucleoside units which occur in the order deoxadenosine-deoxyguanosine-deoxyquanosine-deoxyadenosine-deoxyguanosine-deoxyquanosinethymidine are linked in a 3'→5' manner by methylphosphonate groups. The configuraitons of the methylphosphonate groups are not specified.

The following description will now be given of the synthesis of a particular series of oligodeoxyribonucleoside methyl phosphonates and their physical properties.

The synthetic procedure resulted in the separation of two diastereoisomers of each dimer analog. This synthetic scheme also allowed the preparation of analogs containing a $^{13}$C-enriched phosphonate methyl group. The influence of backbone configuration on overall dimer conformation was studied by ultraviolet, circular dichroism and $^1$H, $^{13}$C and $^{31}$P nuclear magnetic resonance techniques and the results were compared to the conformations of their parent dideoxyribonucleoside monophosphates. Furthermore, the effects of backbone configuration and the removal of the negative charge on the interaction of deoxyadenosine-containing dimers with polyuridylic acid and polythymidylic acid were assessed.

Several processes or methods will now be described for synthesis of the various materials of this invention.

Figure 4:
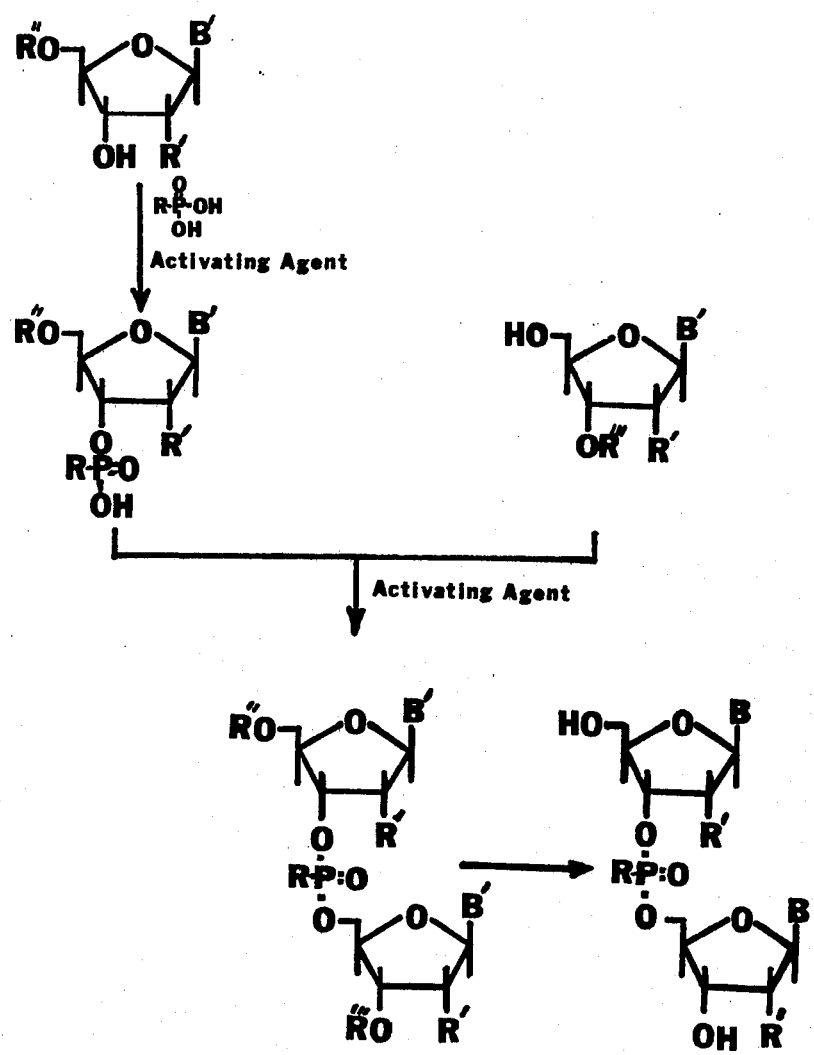
FIG. 4 is a schematic of a process for the synthesis of a dinucleoside alkyl or arylphosphonate.

FIG. 4 shows the synthesis of a dinucleoside alkyl or arylphosphonate. This process consists of esterification of a 5'-O-protected nucleoside having 3'-hydroxyl group with an alkyl or arylphosphonic acid in the presence of an activating agent to form a 5'-O-protected nucleoside-3'-O-alkyl or arylphosphonate.

The latter compound is then esterified with a 3'-O-protected nucleoside having a 5'-hydroxyl group in the presence of an activating agent to form a fully protected dinucleoside alkyl or arylphosphonate. The protecting groups are then removed from the fully protected dinucleoside alkyl or arylphosphonate to form the dinucleoside alkyl or arylphosphonate.

Figure 5:
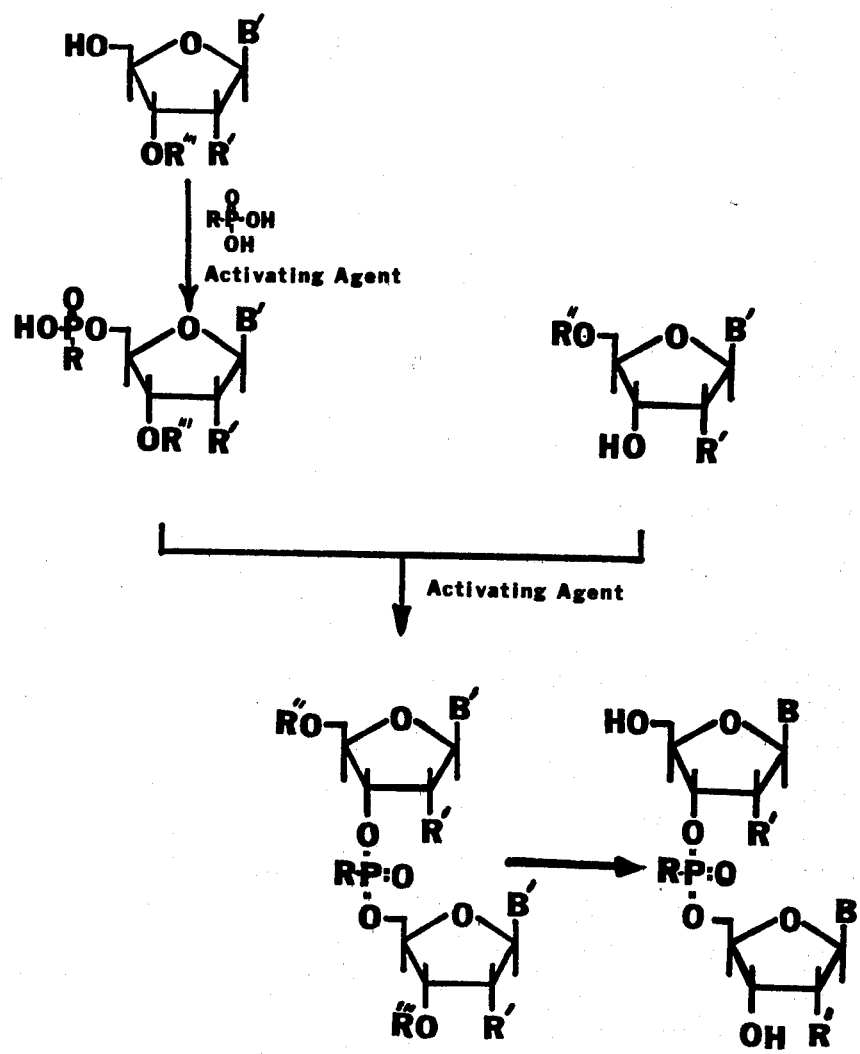
FIG. 5 is a schematic of a process for the synthesis of a dinucleoside alkyl or arylphosphonate.

Referring now to FIG. 5, there is illustated the synthesis of a dinucleoside alkyl or arylphosphonate. This process consists of esterification of a 3'-O-protected nucleoside having a 5'-hydroxyl group with an alkyl or arylphosphonic acid in the presence of an activating agent to form a 3'-O-protected nucleoside-5'-O-alkyl or arylphosphonate.

The latter compound is then esterified with a 5'-O-protected nucleoside having a 3'-hydroxyl group in the presence of an activating agent to form a fully protected dinucleoside alkyl or arylphosphonate. The protecting groups are then removed from the fully protected dinucleoside alkyl or arylphosphonate to form the dinucleoside alkyl or arylphosphonate.

Figure 6:
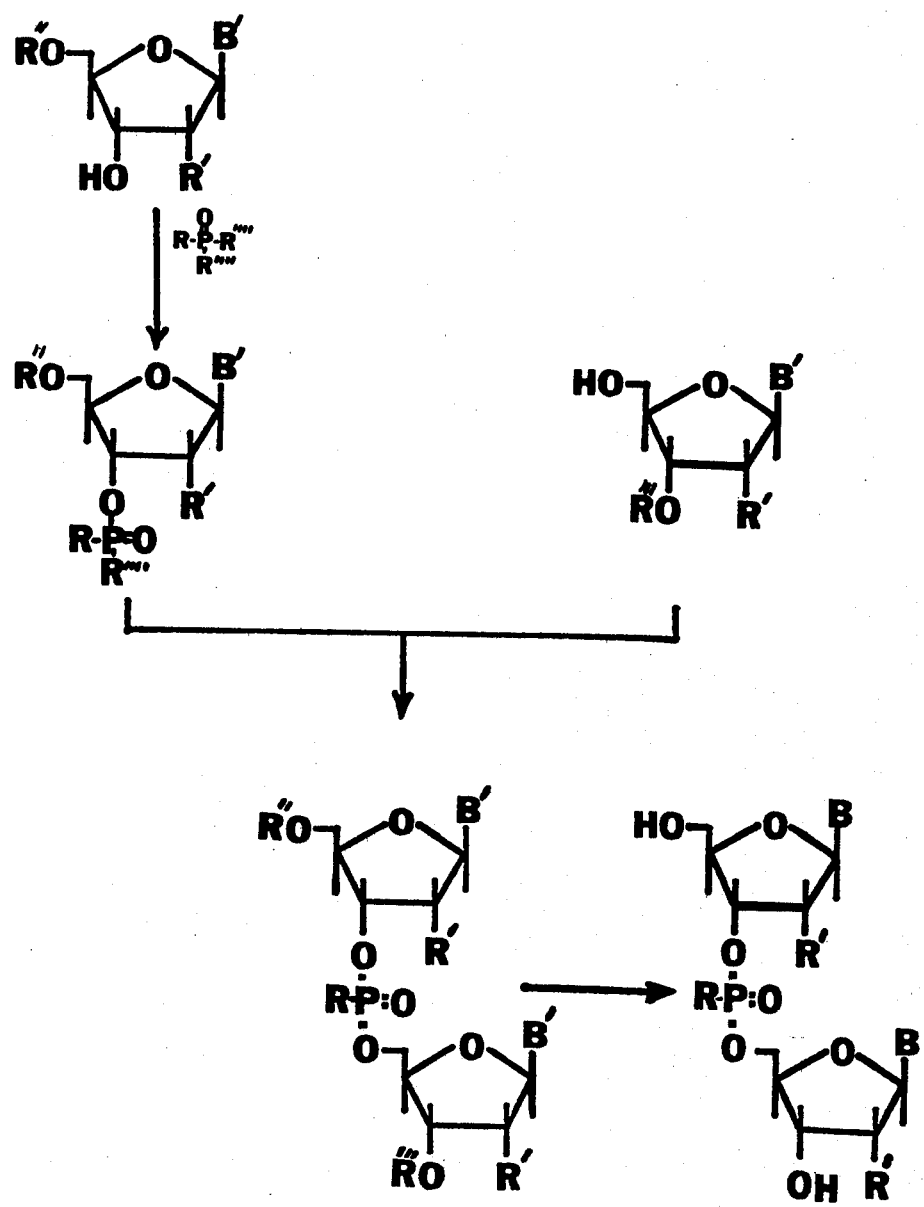
FIG. 6 is a schematic of a process for the synthesis of a dinucleoside alkyl or arylphosphonate.

FIG. 6 shows the synthesis of a dinucleoside alkyl or arylphosphonate. This process consists of esterification of a 5'-O-protected nucleoside having a 3'-hydroxyl group with disubstituted alkyl or arylphosphonate. The substitutents (R'''') can be chloride, imidazolide, triazolide or tetrazolide.

A 5'-O-protected nucleoside-3'-O-monosubstituted alkyl or arylphosphonate is formed in this reaction. This compound is then esterified with a 3'-protected nucleoside having a 5'-hydroxyl group to give the fully protected dinucleoside alkyl or arylphosphonate. The protecting groups are then removed from the fully protected dinucleoside alkyl or arylphosphonate to form the dinucleoside alkyl or arylphosphonate.

Figure 7:
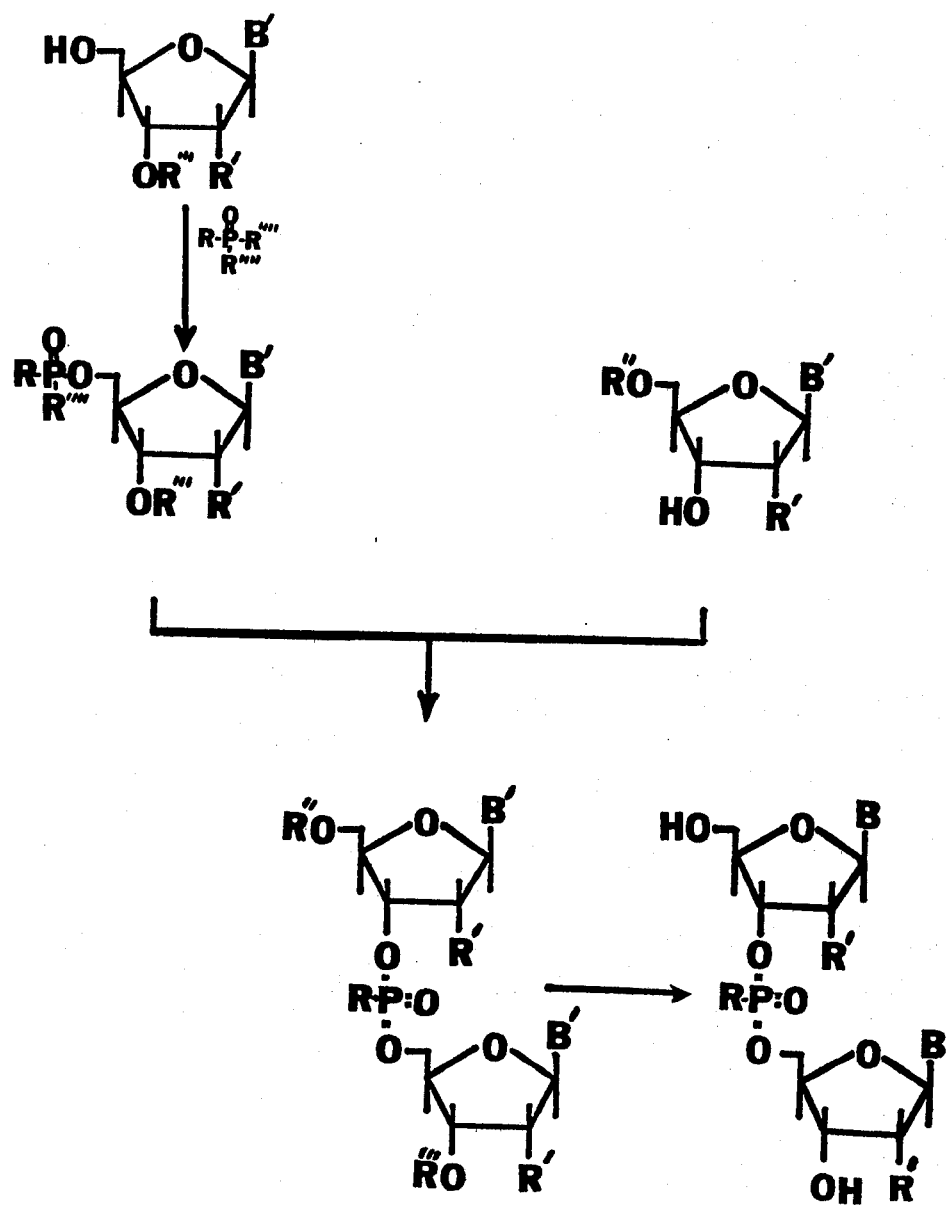
FIG. 7 is a schematic of a process for the synthesis of a dinucleoside alkyl or arylphosphonate.

The synthesis of a dinucleoside alkyl or arylphosphonate is shown in FIG. 7. This process consists in the esterification of a 3'-O-protected nucleoside having a 5'-hydroxyl group with disubstituted alkyl or arylphosphonate. The substituents (R'''') can be chloride, imidazolide, triazolide or tetrazolide. A 3'-O-protected nucleoside-5'-O-monosubstituted alkyl or arylphosphonate is formed in this reaction.

This compound is then esterified with a 5'-protected nucleoside having a 3'-hydroxyl group to give the fully protected dinucleoside alkyl or arylphosphonate. The protecting groups are then removed from the fully protected dinucleoside alkyl or arylphosphonate to form the dinucleoside alkyl or arylphosphonate.

Figure 8:
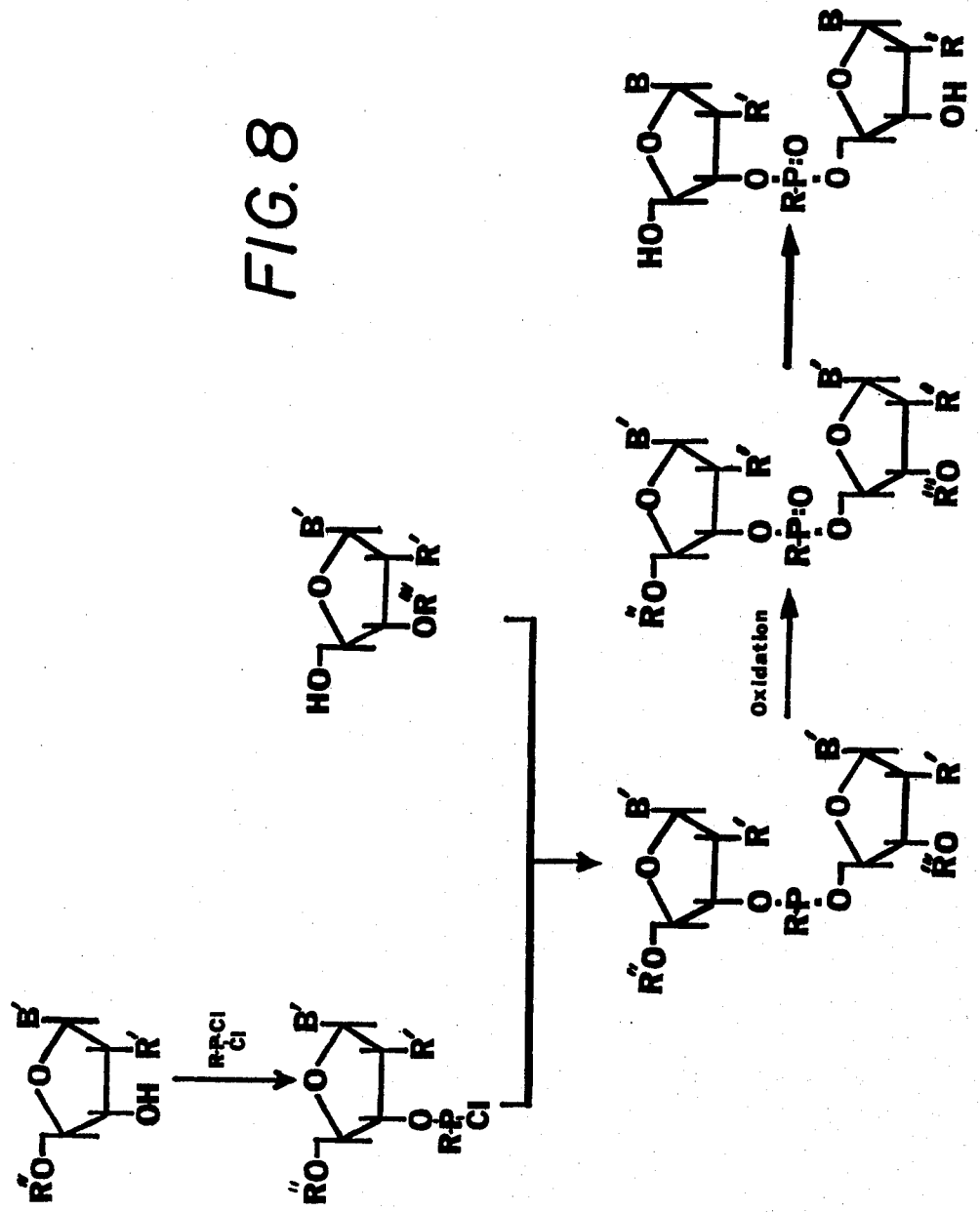
FIG. 8 illustrates the process for the synthesis of a dinucleoside alkyl or arylphosphonate.

FIG. 8 illustrates the synthesis of a dinucleoside alkyl or arylphosphonate. In this process a 5'-O-protected nucleoside having a 3'-hydroxyl group is reacted with a dichloro alkyl or arylphosphine to form a 5'-O-protected nucleoside-3'-O-monochloro alkyl or arylphosphonate.

This compound is then reacted with a 3'-O-protected nucleoside having a 5'-hydroxyl group to give a fully protected dinucleoside alkyl or arylphosphonate.

The latter compound is then oxidized to form a fully protected dinucleoside alkyl or arylphosphonate. The protecting groups are then removed from the fully protected dinucleoside alkyl or arylphosphonate to give the dinucleoside alkyl or arylphosphonate.

Figure 9:
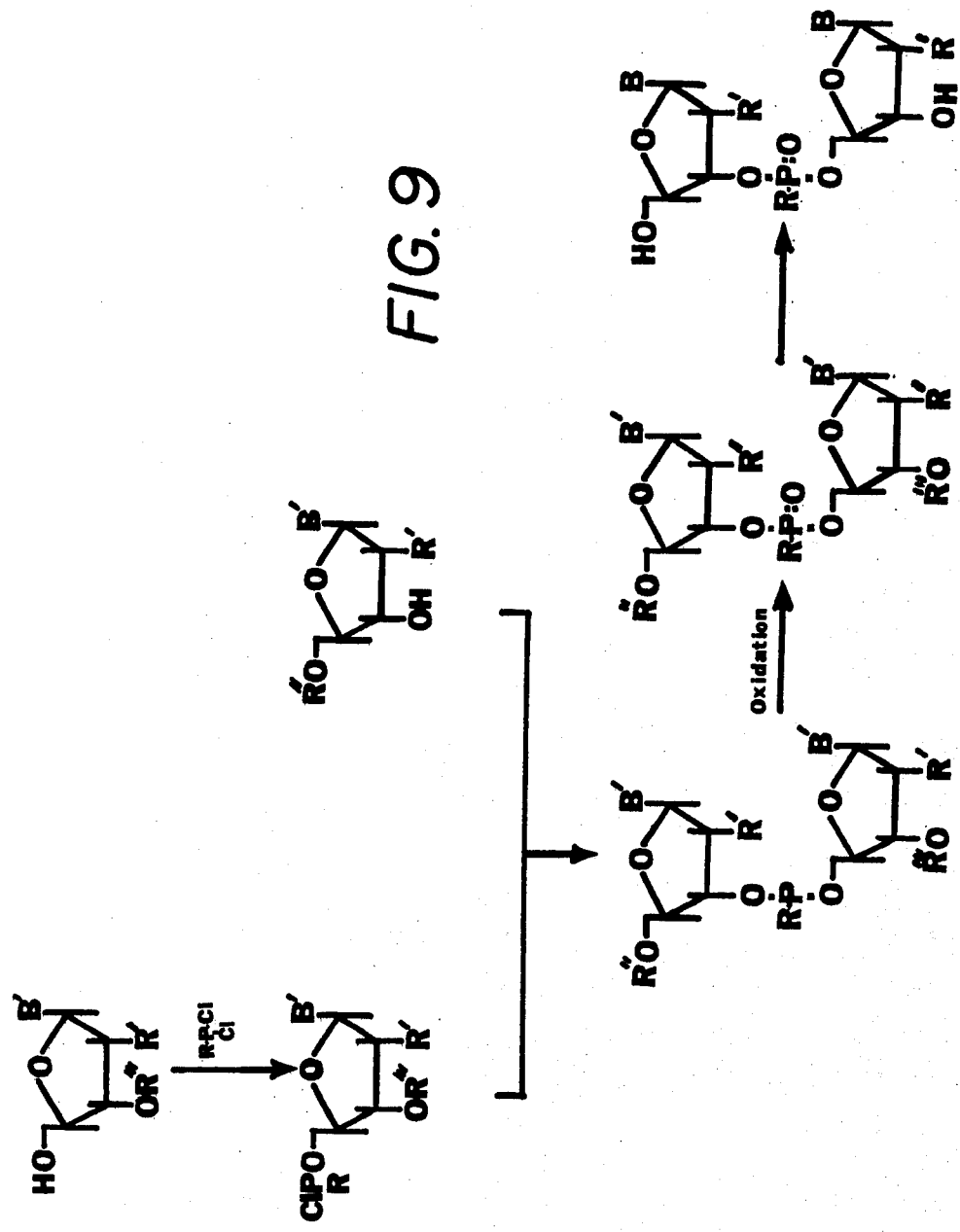
FIG. 9 illustrates the process for the synthesis of a dinucleoside alkyl or arylphosphonate.

FIG. 9 shows the synthesis of a dinucleoside alkyl or arylphosphonate. In this process, a 3'-O-protected nucleoside having a 5'-hydroxyl group is first reacted with a dichloro alkyl or arylphosphine to form a 3'-O-protected nucleoside-5'-O-monochloro alkyl or arylphosphonate.

This compound is next reacted with a 5'-O-protected nucleoside having a 3'-hydroxyl group to give a fully protected dinucleoside alkyl or arylphosphinate. The latter compound is then oxidized to form a fully protected dinucleoside alkyl or arylphosphonate.

The protecting groups are then removed from the fully protected dinucleoside alkyl or arylphosphonate to give the dinucleoside alkyl or arylphosphonate.

Figure 10:
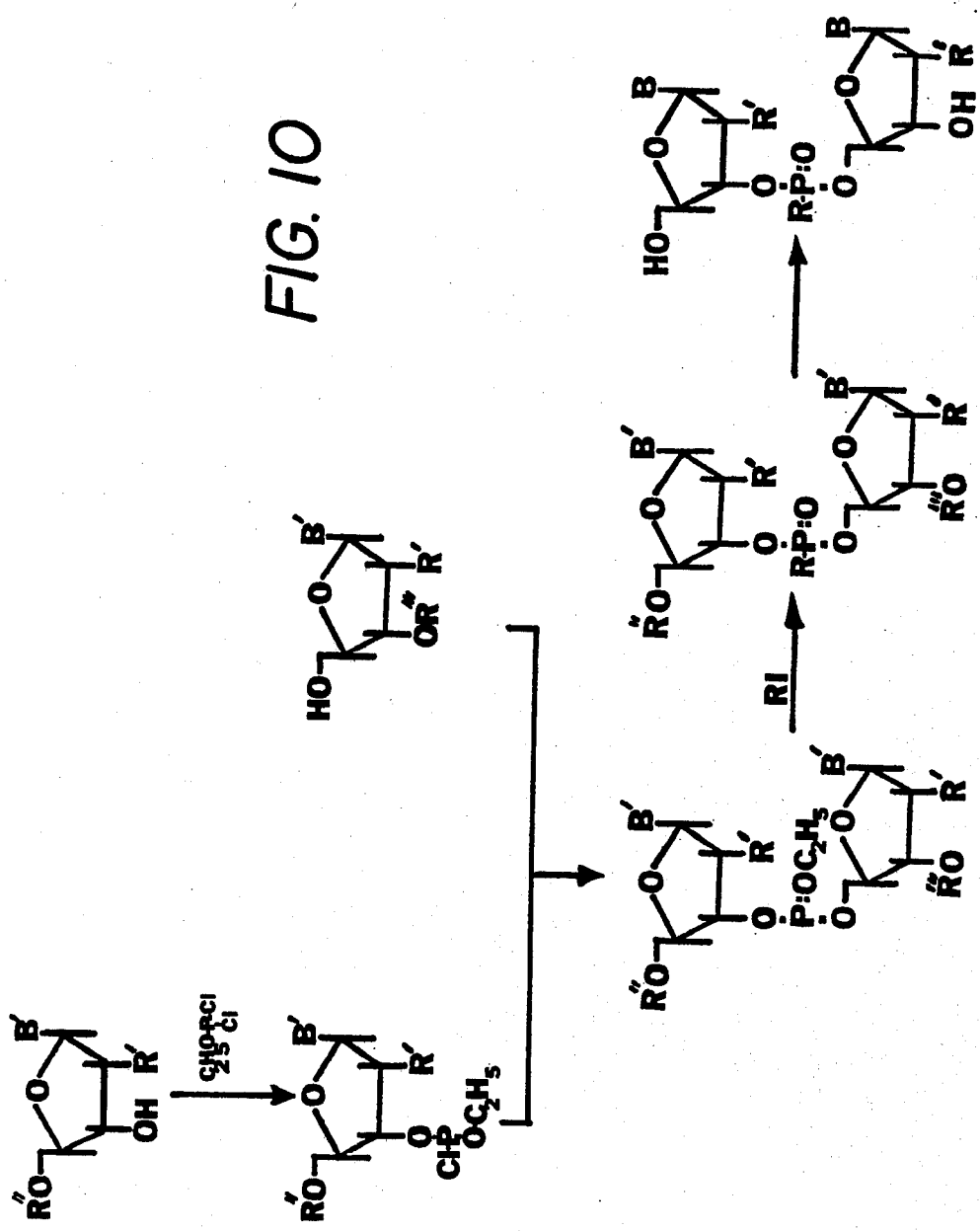
FIG. 10 shows a process for the synthesis of a dinucleoside alkyl or arylphosphonate.

FIG. 10 shows the synthesis of a dinucleoside alkyl or arylphosphonate. In this process, a 5'-O-protected nucleoside having a 3'-hydroxyl group is first reacted with ethyldichlorophosphite to give a 5'-O-protected nucleoside-3'-O-ethyl monochlorophosphite.

This compound is then reacted with a 3'-O-protected nucleoside having a 5'-hydroxyl group to give a fully protected dinucleoside ethylphosphite. The latter compound is then reacted with an alkyl or aryliodide to give a fully protected dinucleoside alkyl or arylphosphonate. The protecting groups are then removed from the fully protected dinucleoside alkyl or arylphosphonate to give the dinucleoside alkyl or arylphosphonate.

Figure 11:
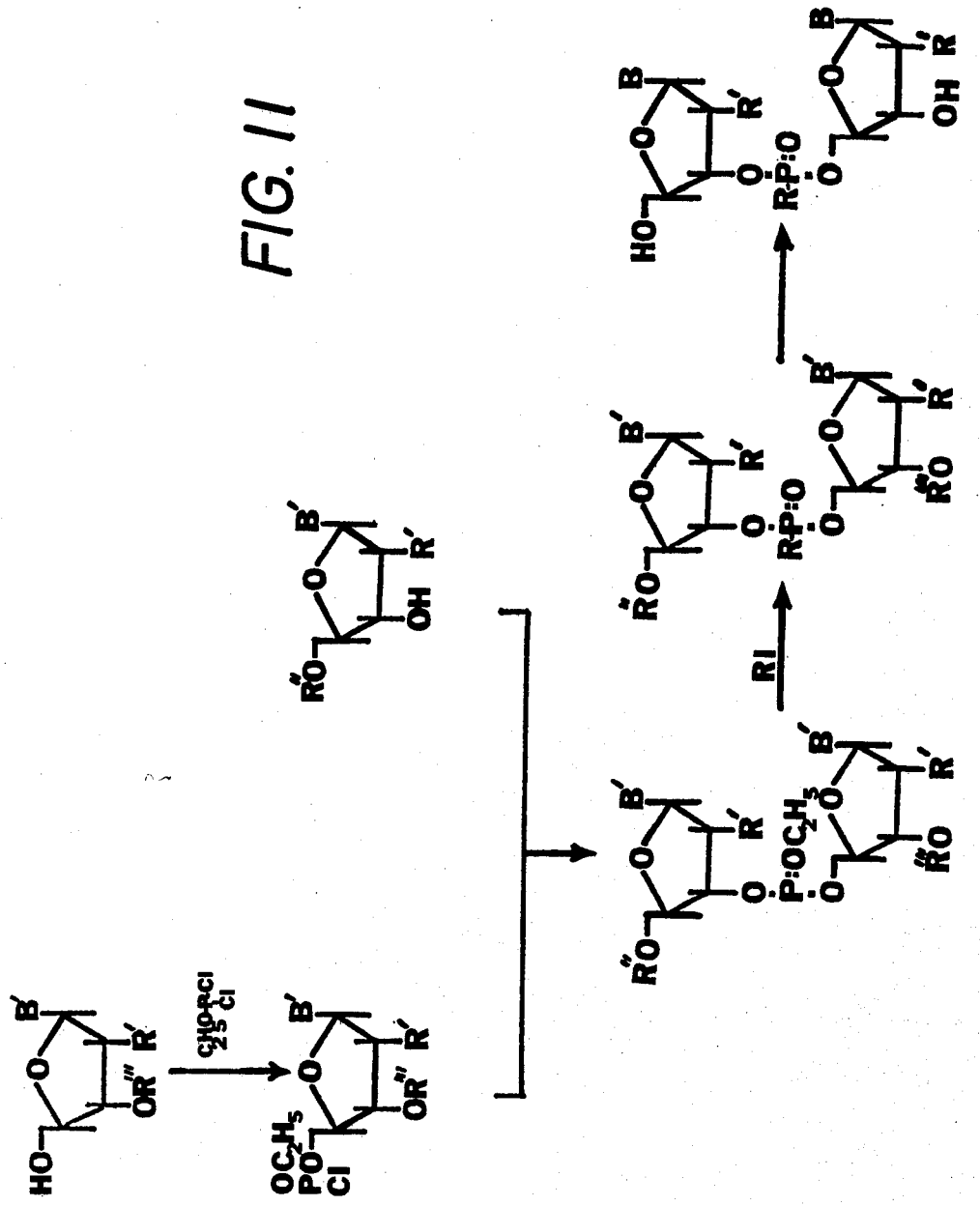
FIG. 11 illustrates the process for synthesis of a dinucleoside alkyl or arylphosphonate.

FIG. 11 shows the synthesis of a dinucleoside alkyl or arylphosphonate. In this process, a 3'-O-protected nucleoside having a 5'-hydroxyl group is reacted with ethyldichlorophosphite to give a 3'-O-protected nucleoside-5'-O-ethyl monochlorophosphite. This compound is reacted with a 5'-O-protected nucleoside having a 3'-hydroxyl group to give a fully protected dinucleoside ethylphosphite. The latter compound is then reacted with an alkyl or aryliodide to give a fully protected dinucleoside alkyl or arylphosphonate. The protecting groups are then removed from the fully protected dinucleoside alkyl or arylphosphonate to give the dinucleoside alkyl or arylphosphonate.

In previous processes (FIGS. 4 to 11), there was described several methods for joining nucleosides to form dinucleoside alkyl or aryl phosphonates. The chain length can be extended from at least 2 to a finite number of greater than 2, for example up to 20. For rapid and efficient synthesis oligonucleoside alkyl or aryl phosphonates can be joined by processes analogous to there previously described for the preparation of dinucleoside alkyl or aryl phosphonates.

Materials and Methods

Thymidine and 2'-deoxyadenosine were checked for purity by paper chromatography before use. 5'-Mono-p-methoxytrityl thymidine, 5'-di-p-methoxy-trityl-N-benzoyldeoxyadenosine, 3'-O-acetylthymidine and 3'-O-acetyl-N-benzoyldeoxyadenosine were prepared according to published procedures.

Diethyl [$^{13}$C]-methyl phosphonate was prepared by reaction of [$^{13}$C]-methyl iodide (96% enriched) with triethyl phosphate followed by vacuum distillation of the product (b.p. 64°–66°/2 mm/Hg. The pyridinium salt of methyl phosphonic acid was prepared by hydrolysis of dimethyl methylphosphonate or diethyl [$^{13}$C]-methyl phosphonate in 4N hydrochloric acid followed by isolation of the product as the barium salt.

The barium salt was converted to the pyridinium salt by passage through a Dowex 50X pyridinium ion-exchange column. Mesitylenesulfonyl chloride was treated with activated charcoal and recrystallized from pentane immediately before use. 1-H-Tetrazole was then prepared. All solvents and reagents were purified.

Silica gel column chromatography was performed using Baker 3405 silica gel (60–200 mesh). Thin layer silica gel chromatography and thin layer cellulose chromatography were done. Paper chromatography was carried out on Whatmann 3 MM paper using the following solvent systems: solvent A, 2-propanol-concd. ammonium hydroxide-water (7:1:2 v/v); solvent C, 1M ammonium acetate-95% ethanol (3:7, v/v); solvent F, 1-propanol-concd. ammonium hydroxide-water (50:10:35, v/v) or solvent I, 2-propanol-water (7:3, v/v).

High pressure liquid chromatography was performed using columns (2.1 mm × 1 m) packed with DuPont Permaphase ODS reverse phase material. Linear gradients (40 ml) from 0% to 75% methanol in water were used at a flow rate of 1 ml/min. The HPLC mobility refers to the percentage of methanol in water required to elute the compound from the column.

For reactions carried out in pyridine, the reactants were dried by repeated evaporation with anhydrous pyridine and were then dissolved in anhydrous pyridine. Unless otherwise noted, all reactions and operations were performed at room temperature.

Preparation of Mesitylenesulfonyl Tetrazolide

Although the preparation of MST has been published, a modified procedure was used. A solution of 1-H-tetrazole (3.36 g: 48 mmoles) in 40 ml of dry methylene chloride containing 5.6 ml (40 mmoles) of triethylamine was added dropwise to 40 ml of anhydrous ether containing mesitylenesulfonyl chloride (8.76 g, 40 mmoles) at room temperature. After 2 hrs, the precipitated triethylammonium chloride was removed by filtration, and washed with 50 ml of methylene chloride-ethyl ether (1:1 v/v).

The filtrate was cooled to 0° C. and pentane was added until the solution became cloudy. This procedure was repeated until a total volume of 25 ml had been added over a 4 hour period. After storage overnight at 4°, the resulting white solid was removed by filtration on a sintered glass filter. The solid was dissolved in 500 ml of anhydrous ethyl ether.

The solution was then filtered to remove a small amount of insoluble material. The filtrate was evaporated to dryness and the resulting mestilylene sulfonyl tetrazolide (4.46 g) was obtained in 44% yield. The MST was pure as indicated by silica gel tlc, Rf ($C_6H_6$) 0.11 (m.p. 109°–110° C.) and was stored in a desicator at −80° C. Under these storage conditions, the MST maintained its condensing activity for at least one month.

Preparation of [MeOTr]TpCE

[MeOTr]T (10.3 g, 20 mmoles), the pyridinium salt of methyl phosphonic acid (40 mmoles) and Dowex pyridinium resin (0.5 g) were treated with dicyclohexyl-carbodiimide (41.2 g, 200 mmoles) in 100 ml of pyridine at 37° C. for 3 days. The resulting [MeOTr]Tp, Rf silica gel tlc 0.00 (EtOAc/THF 1:1), appeared to be formed in approximately 86% yield as determined by HPLC. The material is eluted from the HPLC column with 37% methanol/water.

Hydracrylonitrile (100 ml) was added to the reaction mixture, which was kept at 37° C. for 2 days. Aqueous pyridine (200 ml) was then added and the resulting dicyclohexylurea was removed by filtration. The filtrate was evaporated, dissolved in 250 ml of ethyl acetate and the solution extracted with 3 (250 ml) portions of water. The ethyl acetate solution was dried over anhydrous sodium sulfate. After filtration and evaporation, the mixture was chromatographed on a silica gel column (5.4 × 37 cm) which was eluted with ether (1L), ethyl acetate (1.2 L) and tetrahydrofuran (1.6 L). Pure [MeOTr]TpCE (7.5 g) was isolated in 55% yield after precipitation from tetrahydrofuran by addition of hexane. The monomer has Rf values of 0.32 (EtOAc/THF 1:1) and 0.66 (20% MeOH-CHCl$_3$) on silica gel tlc and is eluted from the HPLC column with 54% methanol/water. The UV spectrum gave λ max 267 nm, sh 230 nm, λ min 250 nm, $\epsilon_{260}/\epsilon_{280}$ 1.44 in 95% ethanol.

Preparation of [MeOTr]Tp Pyridinium Salt

[MeOTr]TpCE (2.17 g, 3.36 mmoles) was treated with 16.8 ml of 1N sodium hydroxide in a solution containing 126 ml of dioxane and 25 ml of water for 15 min. The solution was neutralized by addition of Dowex 50X pyridinium resin. After filtration, the solution was evaporated and the residue was rendered anhydrous by evaporation with pyridine. The [MeOTr]Tp (1.90 g; 2.83 mmoles) was obtained in 84% yield after precipitation from pyridine by addition to anhydrous ether. The material has Rf values of 0.00 (EtOAc/THF 1:1) and 0.04 (20% MeOH/CHCl$_3$) on silica gel tlc. The UV spectrum gave λ max 267 nm, sh 230 nm, λ min 250 nm, $\epsilon_{230}/\epsilon_{267}$ 1.68, $\epsilon_{260}/\epsilon_{280}$ 1.44 in 95% ethanol.

The monomethoxytrityl group was removed from 70 mg (0.1 mmole) of d-[(MeO)Tr]Tp by treatment with 80% aqueous acetic acid. The resulting Tp (874 A$_{267}$ units, 0.095 mmole) was isolated in 95% yield by chromatography on a DEAE Sephadex A25 column (3 × 8.5 cm) using a linear gradient of ammonium bicarbonate (0.01M to 0.20M, 500 ml). The monomer has the following Rf values on cellulose TLC:0.41 (solvent A), 0.77

(solvent C) and 0.69 (solvent F). The UV spectrum gave λ max 267 nm, λ min 235 nm in water pH 7.0. The pmr spectrum was consistent with the structure of the monomer.

Preparation of TpCE

[MeOTr]TpCE (3.26 g, 5.04 mmoles) dissolved in 20 ml of methanol was treated with 80 ml of 80% acetic acid solution for 5 hr. at 37° C. The solvents were removed by evaporation and the residue was evaporated repeatedly with 50% toluenetetrahydrofuran to remove the acetic acid. TpCE (1.80 g, 4.8 mmoles) was obtained in 96% yield after precipitation from tetrahydrofuran (10 ml) by addition of hexane (200 ml). The material has Rf values of 0.08 (EtOAc/THF, 1:1) and 0.16 (15% MeOH/CHCl$_3$) on silica gel tlc. The UV spectrum gave λ max 265 nm, λ min 233 nm, ε260/ε280 1.61 in absolute ethanol.

Preparation of d-[(MeO)$_2$Tr]bzApCE

A solution containing d-[MeO)$_2$Tr]bzA (10.5 g; 16 mmoles), methyl phosphonic acid (32 mmoles) and Dowex 50X pyridinium resin (0.5 g) in 80 ml of anhydrous pyridine was treated with dicyclohexylcarbodiimide (25 g; 121 mmoles) for 3 days at 37° C. Examination of the reaction mixture by HPLC showed essentially quantitative conversion of d-[(MeO)$_2$Tr]bzA to d-[(MeO)$_2$Tr]bzAp, which has HPLC retention time of 22.8 min. The reaction mixture was treated with 80 ml of hydracrylonitrile for 2 days at 37° C.

After filtration and evaporation of the solvents, the residue was dissolved in 200 ml of ethyl acetate and the solution was extracted with three (200 ml) portions of water. The ethyl acetate solution was dried over anhydrous sodium sulfate, concentrated to 50 ml and chromatographed on a silica gel column (5.4×37 cm).

The column was eluted with ether (1.5 L), ethyl acetate (1.5 L) and tetrahydrofuran (1.5 L). The resulting d-[(MeO)$_2$Tr]bzApCE weighed 5.4 g (6.84 mmoles, 43%) after precipitation from tetrahydrofuran (100 ml) with hexane (500 ml). The material elutes from the HPLC column with 68% methanol/water, and has silica gel TLC Rf values of 0.13 (EtOAc/THF, 1:1 v/v) and 0.27 (THF). The UV spectrum shows λ max 279 nm and 234 nm, λ min 258 nm and 223 nm; ε234/ε279 1.44, ε260/ε280 0.67, in 95% ethanol.

Preparation of d-[(MeO)$_2$Tr]bzAp

A solution containing d-[(MeO)$_2$Tr]bzApCE (3.79 g, 4.8 mmoles) in 180 ml of dioxane and 36 ml of water was treated with 24 ml of 1N sodium hydroxide for 7 min. The solution was neutralized with Dowex 50X pyridinium resin and then was passed through a Dowex 50X pyridinium ion exchange column (3×30 cm). The eluate was evaporated and the residue was rendered anhydrous by evaporation with pyridine. The resulting d-[(MeO)$_2$Tr]bzAp (2.9 g; 3.56 mmoles) was obtained in 74% yield after precipitation from anhydrous ether. The material has Rf values of 0.00 (THF) and 0.36 (50% MeOH/CHCl$_3$) on silica gel tlc. The UV spectrum showed λ max 280 nm and 233 nm, λ min 255 nm and 225 nm ε233/ε280 1.37, ε260/ε280 0.67 in 95% ethanol.

The protecting groups were removed from a small sample of d-[(MeO)$_2$Tr]bzAp (80 mg, 0.1 mmole) by sequential treatment with concentrated ammonium hydroxide in pyridine and 80% acetic acid. The monomer dAp (1400 A$_{260}$ units, 0.09 mmole) was isolated by chromatography on a DEAE Sephadex A-25 column (3×8.5 cm) using a linear gradient of ammonium bicarbonate (0.01 to 0.2M, 600 ml). The monomer has the following Rf values on cellulose TLC:0.45 (solvent A), 0.56 (solvent C) 0.67 (solvent F) and 0.44 (solvent I). The UV spectrum showed λ max 259 nm, λ min 227 nm 260/280 6.13, in water pH 7.0. The pmr spectrum was consistent with the structure of the monomer.

Preparation of d-bzApCE

A solution of d-[(MeO)$_2$Tr]bzApCE (1.58 g, 2 mmoles) in 6.3 ml of methanol was treated with 25 ml of 80% acetic acid for 1.5 hrs. The solvents were evaporated and the residue was repeatedly evaporated with toluene and tetrahydrofuran to remove acetic acid. The residue was precipitated from 20 ml of tetrahydrofuran by dropwise addition to 250 ml of hexane to give 0.95 g (1.95 mmoles) of d-bzApCE in 98% yield. The material has Rf values of 0.09 (THF) and 0.25 (20% MeOH/CHCl$_3$) on silica gel TLC and is eluted from the HPLC column with 12% methanol/water. The UV spectrum shows λ max 280 nm, sh 233 nm, λ min 247 nm ε233/ε280 0.65 ε260/ε280 0.60, in 95% ethanol.

Preparation of Dinucleoside Methyl Phosphonates

The general procedure for the preparation of protected dinucleoside methyl phosphonates is given in this section. Table 1 shows the specific reaction conditions and yields for each dimer. The protected nucleoside 3'-methyl phosphonate and protected nucleoside or nucleoside 3'-methyl phosphonate cyanoethyl ester were dried by evaporation with anhydrous pyridine. The condensing agent was added and the reactants were taken up in anhydrous pyridine to give a 0.2M solution. After completion of the reaction as indicated by TLC and/or HPLC, an equal volume of water was added and the solution was kept at room temperature for 30 min. The solvents were then evaporated and the residue dissolved in ethyl acetate or chloroform. The organic solution was extracted with water and then dried over anhydrous sodium sulfate. After concentration, the organic solution was applied to a silica get column (3×28 cm for a 1 mmole scale reaction). The column was eluted with ethyl acetate, ethyl acetate/tetrahydrofuran (1:1 v/v) and tetrahydrofuran. The progress of the elution was monitored by silica get TLC. Dimers terminating with a 3'-acetyl group separated into their individual diastereoisomers on the column and were eluted as pure isomer 1, a mixture of isomer 1 and 2 and pure isomer 2. The dimers were isolated as white solids, by precipitation from tetrahydrofuran solution upon addition of hexane. The Rf values on silica get tlc, the mobilities on the HPLC column and the ultraviolet spectral characteristics of the protected dimers are given in Table 2.

TABLE 1

| Preparation of Protected Dideoxyribonucleoside Methyl Phosphonates | | | | | |
|---|---|---|---|---|---|
| Monomers (mmole) | | Condensing Agent[a] (mmole) | Reaction Time | Dimer (mmole) | Yield |
| d-[(MeO)Tr]Tp | (0.20) | DCC | 3 days | d-[(MeO)Tr]TpTOAc | 16% |

TABLE 1-continued

Preparation of Protected Dideoxyribonucleoside Methyl Phosphonates

| Monomers (mmole) | | Condensing Agent[a] (mmole) | Reaction Time | Dimer (mmole) | Yield |
|---|---|---|---|---|---|
| + d-TOAc | (0.22) | (0.73) | 37° C. | (0.031) | |
| d-[(MeO)Tr]Tp | (2.40) | MST | 3 hrs. | d-[(MeO)Tr]TpTpCE | 55% |
| + d-TpCE | (3.60) | (9.60) | r.t. | (1.32) | |
| d-[(MeO)₂Tr]bzAp | (1.26) | TPSCl | 4 days | d-[(MeO)₂Tr]bzApbzAOAc | 39% |
| + d-bzAOAc | (1.50) | (2.0) | 37° C. | (0.50) | |
| d-[(MeO)₂Tr]bzA- | (0.70) | MST | 4 hrs. | d-[(MeO)₂Tr]bzA-[¹³C]—pbzAOAc | 41% |
| [¹³C]—p + d-bzAOAc | (1.05) | (2.8) | r.t. | (0.29) | |
| d-[(MeO)₂Tr]bzAp | (0.85) | MST | 6 hrs. | d-[(MeO)₂Tr]bzApbzApCE | 46% |
| + d-bzApCE | (1.28) | (4.0) | r.t. | (0.39) | |
| d-[(MeO)Tr]Tp | (1.0) | TPSCl | 16 hrs. | d-[(MeO)tr]TpbzAOAc | 35% |
| + d-bzAOAc | (1.0) | (3.0) | 37° C. | (0.35) | |
| d-[(MeO)₂Tr]bzAp | (1.0) | TPSCl | 46 hrs. | d-[(MeO)₂Tr]bzApTOAc | 38% |
| + d-TOAc | (1.3) | (1.5) | 37° C. | (0.38) | |

[a]DCC — dicyclohexylcarbodiimide
TPSCl — triisopropylbenzenesulfonyl chloride
MST — mesitylenesulfonyl tetrazolide The base labile protecting groups were removed from the dimers by treatment with 50% concentrated ammonium hydroxide-pyridine solution for 3 days at 4° C. Alternatively, the N-benzoyl protecting groups of dimers containing deoxyadenosine could be removed by treatment with 85% hydrazine hydrate in 20% acetic acid-pyridine buffer overnight at room temperature (Letsinger et al., 1968). This treatment also partially removed the 3'-O-acetyl group. The acetyl group was completely removed by further treatment with 50% concentrated ammonium hydroxide-pyridine solution for 2 hours at 4° C. After complete removal of solvents, the trityl protecting groups were removed by treatment with 80% acetic acid-methanol (8:2 v/v) solution at room temperature. The solvents were then removed and the dimers were chromatographed on Whatmann 3 MM paper using solvent A. The dimers were eluted from the paper with 50% aqueous ethanol. For dimers terminating with 3'-OH groups, the ethanol solutions were passed through small (0.5×1 cm) DEAD cellulose columns to remove trace impurities eluted from the paper chromatogram.

Dimers terminating with 3'-methyl phosphonate groups were absorbed to small DEAE cellulose columns and then eluted with 0.5M ammonium bicarbonate solution. The dimers were stored as standard solutions in 50% ethanol at 0° C., and were found to be complete stable under these conditions for at least 9 months. For physical and nmr studies, aliquots containing the required amount of dimer were evaporated to remove the ethanol and then lyophilized from water or D₂O before use. The Rf values and UV spectral characteristics of the dimers are given in Table 3. The pmr spectra and tentative chemical shift assignments of the two diastereoisomers of d-ApA and d-TpT are shown in FIG. 12.

TABLE 2

Chromatographic Mobilities and Ultraviolet Spectral Properties of Protected Dideoxyribonucleoside Methyl Phosphonates

| Dimer | Mobility (Rf) Silica Gel TLC[a] | | HPLC Mobility[c] (% methanol water) | Ultraviolet Spectral Properties[b] | | |
|---|---|---|---|---|---|---|
| | 10% MeOH/ THF CHCl₃ | 15% MeOH/ CHCl₃ | | λ max (nm) | λ min (nm) | |
| d-[(MeO)Tr]TpTOAc | 0.44 | 0.63 0.53 | — | — | 267sh235 | 246 | $\frac{\epsilon235}{\epsilon267} = 0.91$ |
| d-[(MeO)Tr]TpTpCE | — | — | 0.28 0.22 | — | 265sh235 | 245 | $\frac{\epsilon235}{\epsilon265} = 0.93$ |
| d-[(MeO)₂Tr]bzApbzAOAc | 0.34 0.29 | — | 0.51 0.43 | 68% | 281sh233 | 256 | $\frac{\epsilon233}{\epsilon281} = 1.10$ |
| d-[(MeO)₂Tr]bzApbzApCE | 0.09 | 0.32 0.28 | 0.39 0.35 | — | 281sh230 | 256 | $\frac{\epsilon230}{\epsilon281} = 1.24$ |
| d-[(MeO)Tr]TpbzAOAc | 0.47 | 0.24 0.19 | 0.59 | 62% | 276;230, sh260 | 247;227 | $\frac{\epsilon230}{\epsilon276} = 1.07$ |
| d-[(MeO)₂Tr]bzApTOAc | 0.49 0.41 | — | 0.52 0.48 | 66% | 277;235, sh263 | 255,227 | $\frac{\epsilon235}{\epsilon277} = 1.18$ |

[a]Two Rf values refer to the mobilities of the individual diastereoisomers.
[b]Ultraviolet spectra were measured in 95% ethanol at room temperature.
[c]Percentage of methanol in water required to elute compound from HPLC column (DuPont Phermaphase ODS)

TABLE 3

Chromatographic Mobilities and Ultraviolet Spectral Properties of Dideoxyribonucleoside Methyl Phosphonates

| Dimer | Mobility Paper Chromatography | | | Ultraviolet Spectral Properties[a] | | |
|---|---|---|---|---|---|---|
| | Rf(A) | Rf(C) | Rf(I) | λ max (nm) | λ min (nm) | ε260/ε280 |
| d-TpT | — | 0.67 | 0.73 | 267 | 234 | 1.91 |
| d-ApA | — | 0.48 | 0.62 | 258 | 223 | 6.65 |
| d-ApAp | 0.30 | — | 0.38 | 258 | 227 | 4.52 |
| d-TpA | 0.42 | 0.57 | 0.63 | 262 | 230 | 2.80 |
| d-ApT | 0.33 | 0.55 | 0.61 | 261 | 233 | 3.22 |

TABLE 4

Hypochromicity of Dideoxyadenosine Methyl Phosphonate Analogs

| Compound | $\epsilon$(molar)$^{(a)}$ | % Hypochromicity |
| --- | --- | --- |
| dpA | $15.3 \times 10^3$ | — |
| d-ApA | $12.7 \times 10^3$ | 17% |
| (d-ApA)$_1$ | $13.7 \times 10^3$ | 11.0% |
| (d-ApA)$_2$ | $14.3 \times 10^3$ | 7.1% |
| (d-ApAp)$_1$ | $13.0 \times 10^3$ | 13.3% |
| (d-ApAp)$_2$ | $13.3 \times 10^3$ | 11.3% |

$^{(a)}$Measured in 1 mM Tris HCl pH 7.4 at 27° C.

Similar pmr spectra were obtained for d-ApT and d-TpA (data not shown). The spectra are consistent with the structures of the dimers. The complete characterization of all these dimers by pmr spectroscopy will be described in a subsequent paper (Kan et al., manuscript in preparation).

Physical Studies and Interaction with Polynucleotides

Ultraviolet and circular dichroism spectra were recorded respectively on a Cary 15 spectrophotometer and a Cary 60 spectropolarimeter with CD attachment. The continuous variation experiments, melting experiments and circular dichroism experiments were carried out as previously described. The molar extinction coefficient of poly U is $9.2 \times 10^3$ (265 nm) and poly dT is $8.52 \times 10^3$ (264 nm). The molar extinction coefficients of the dideoxyadenosine methyl phosphonates were determined by comparing the absorption of a solution of the dimer at pH 7.4 with the absorption of the same solution at pH 1.0. The dimer extinction coefficient was then calculated from the observed hyperchromicity of the dimer at pH 1.0 using an extinction coefficient for deoxyadenosine at pH 1.0 of $14.1 \times 10^3$.

Preparation of Dinucleoside Methyl Phosphonates

The synthetic route used to prepare the dinucleoside methyl phosphonates has previously been described. 5'-Mono-p-methoxytrityl thymidine and 5'-di-p-methoxytrityl-N-benzoyl deoxyadenosine were converted to the corresponding 3'-methyl phophonate β-cyanoethyl esters (2) by sequential reaction of (1) with methyl phosphonic acid and β-cyanoethanol in the presence of dicyclohexylcarbodiimide.

The preparation of nucleoside 5'-methyl phosphonates by reaction of a suitably protected nucleoside with methyl phosphonic acid has been previously known. Direct conversion of the protected nucleoside-3'-methyl phosphonate to its β-cyanoethyl ester allows purification of this intermediate on a large scale by silica gel column chromatography, thus avoiding the use of ion exchange chromatography. They trityl or β-cyanoethyl protecting groups can be selectively removed from 2 by treatment with either 80% acetic acid or 0.1N sodium hydroxide solution, respectively, at room temperature.

Protected nucleoside-3'-methyl phosphonate (4) was condensed with either 3'-O-acetyl thymidine or 3'-O-acetyl-N-benzoyldeoxyadenosine to give fully protected dinucleoside methyl phosphonate 6. Alternatively, 4 was condensed with the β-cyanoethyl ester of thymidine-3'-methyl phosphonate or N-benzoyldeoxyadenosine-3'-methyl phosphonate to give 7. The condensing agents used in these reactions were dicyclohexylcarbodiimide, triisopropylbenzenesulfonyl chloride or mesitylenesulfonyl tetrazolide. The reaction conditions and yields are given in Table 1.

The fully protected dimers were readily purified by silica gel column chromatography. For dimers terminating with 3'-O-acetyl groups, the two diastereoisomers were sufficiently separated on the silica gel column that fractions containing each pure diastereoisomer were obtained. These isomers were designated isomer 1 and isomer 2 in reference to their order of elution from the column. The diastereoisomers were generally formed in a 4:6 ratio of isomer 1 to isomer 2.

Alternatively, the diastereoisomers could be obtained in pure form by thick layer chromatography on silica gel plates. The dimers terminating in a 3'-O-β-cyanoethyl methyl phosphophonate group (7) consists of four diastereoisomers, although only two separate bands were observed on silica gel thin layer chromatography (see Table 2). For the deoxyadenosine-containing dimer, these two bands turned out to be the two isomers with opposite configuration (axial and equatorial, see FIG. 16) about the methyl phosphonyl internucleoside linkage.

Removal of the protecting groups from 6 and 7 was accomplished by sequential treatment with concentrated ammonium hydroxide in pyridine for 3 days at 4° C. followed by treatment with 80% acetic acid. In the case of the dideoxyadenosine methyl phosphonates, some hydrolysis of the phosphonate linkage was noted when the ammonium hydroxide treatment was carried out at room temperature. However, the hydrolysis was suppressed at low temperature. Alternatively, the N-benzoyl protecting groups of these dimers could be removed by treatment with hydrazine hydrate. The dimers were then purified by paper chromatography. The individual diastereoisomers of each deprotected dimer had the same chromatographic mobilities on paper chromatography in all solvent systems tested (See Table 3).

Ultraviolet and Hypochromicity Measurements

The ultraviolet spectral properties of the dinucleoside methyl phosphonates are recorded in Table 3. Qualitatively, the spectra are similar to those of (3'-5')-linked dinucleoside monophosphates. The spectra of the individual diastereoisomers are qualitatively similar to each other.

Hypochromicity measurements for the dideoxyadenosine methyl phosphonates were carried out in water at pH 7.4 and are shown in Table 4. The percent hypochromicity of the methyl phosphonate dimers is from 4% to 10% lower than the percent hypochromicity of d-ApA. Each diastereoisomer has an unique molar extinction coefficient. The hypochromicity of isomer 1, the isomer eluted first from the silica gel column, is greater that that of isomer 2, reflecting differences in the extent of base-base overlap in these dimers.

Circular Dichroism Spectra

Differences in the extent and mode of base stacking interactions are observed for individual diastereoisomers within a given dimer sequence as reflected by the CD spectra of the dimers. The profile of the CD spectrum of d-ApA)$_1$ (FIG. 13a) is qualitatively similar to that of the parent dinucleoside monophosphate, d-ApA (Miller et al., 1971). However, the magnitudes of the molecular ellipticity ($\theta$) at 267 nm and 270 nm of d-ApA)$_1$ are approximately one-half of those found for d-ApA. A very dramatic difference in the CD spectrum of d-ApA)$_2$ is observed. Only negative [$\theta$] is found at 250 nm and the amplitude of the molecular ellipticity is approximately three-fold less than that of d-ApA)₁. Similar results were observed for d-ApAp)₁ and d-ApAp)₂ (data not shown).

In the case of d-ApT (FIG. 13b), the profiles of the CD spectra of both isomers 1 and 2 are qualitatively similar to that of d-ApT (Cantor et al., 1970). However, the magnitude of the ellipticity of the peak (272 nm) and trough (253 nm) of the dinucleoside methyl phosphonate are less than those in the dinucleoside monophosphate. For d-ApT₁, the peak is reduced 1.8-fold and the trough is reduced 1.3-fold compared to d-ApT while for d-ApT)₂ the reductions are 8.1 and 5.0-fold.

The CD spectra of d-TpA)₁ and d-TpA)₂ (FIG. 13c) show differences in both the magnitude of the molecular ellipticity and in the position of the positive and negative bands. Isomer 2 has a CD spectrum which is virtually identical to that observed for d-TpAp (Cantor et al., 1970). Isomer 1, on the other hand, has a lower magnitude of the ($\theta$) value, while the positions of the peak and trough are shifted to shorter wavelengths.

The CD results for dApT)₁ and 2 and dTpA)₁ and 2 are qualitatively similar to those obtained by others on the CD spectra of the separated diastereoisomers of the dinucleoside ethyl phosphotriesters, dAp(Et)T and dTp(Et)A. In the case of these triesters, one isomer has a spectrum which is almost identical to that of the corresponding dinucleoside monophosphate. The other isomer shows significant reductions in the magnitudes of both the positive and negative CD absorbtion bands. It is not possible at this time to make detailed comparisons between the present results and those on the triesters, since the absolute configurations of the modified phosphate groups in the triesters are not known.

Figure 13:
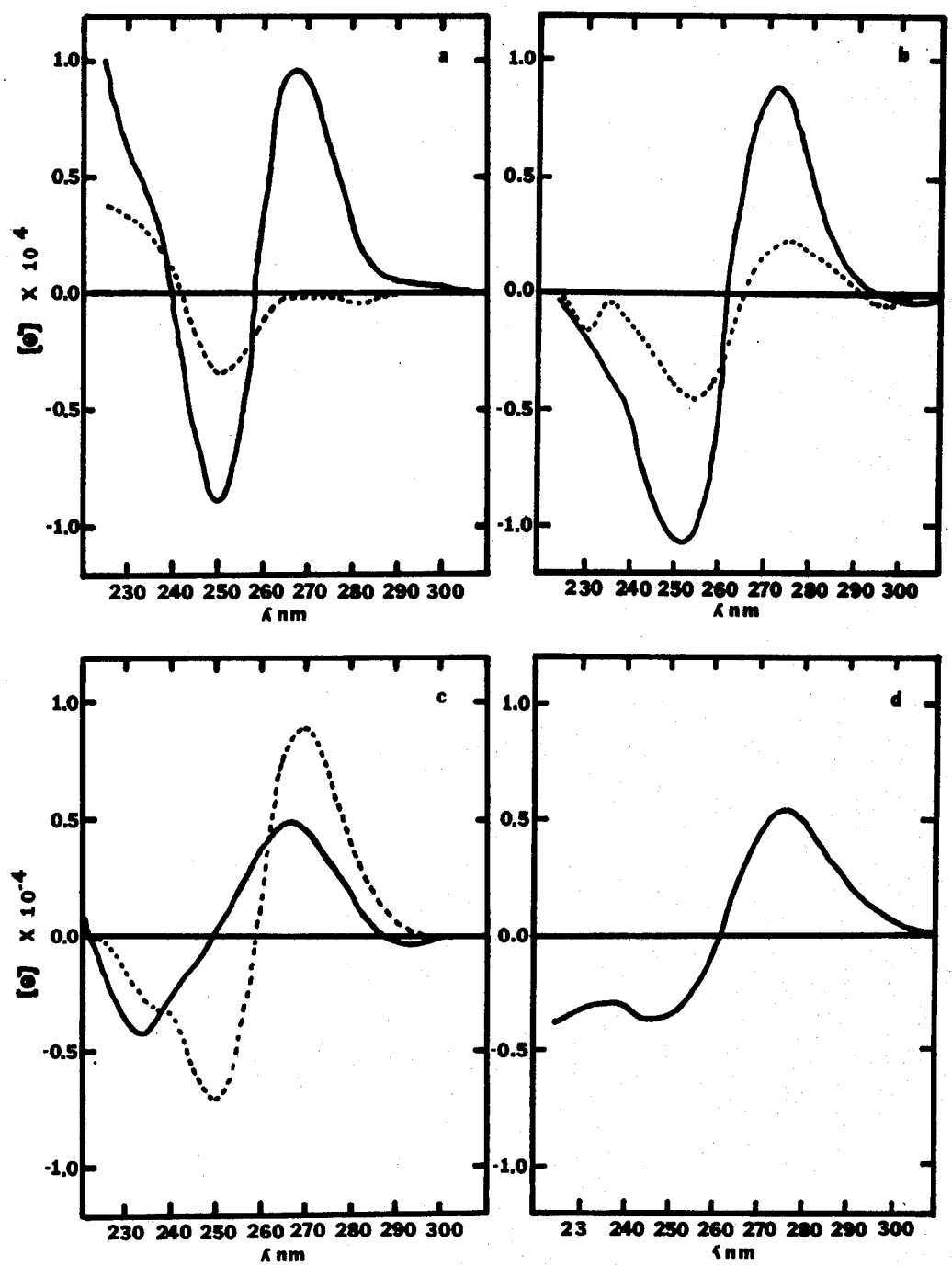
FIG. 13 is spectral diagrams of circular dichroism spectra of (a) dApA)$_1$ (—); dApA)$_2$ (- - -); (b) dApT)$_1$ (—), dApT$_2$ (- - -); (c) dTpA)$_1$ (- - -), dTpA)$_2$ (—); and (d) dTpT in 10 mM Tris.HCl, 10 mM MgCl$_2$, pH 7.5 at 27° C.

FIG. 13d shows the CD spectrum of a 1:1 mixture of the diastereoisomers of d-TpT. The spectrum of this mixture is clearly different than the spectrum of d-TpT (Cantor et al., 1970). For d-TpT positive ($\theta$) occurs at 280 nm with a magnitude approximately 1.8-fold greater than the 275 nm band of d-TpT. Similarly, d-TpT shows negative ($\theta$) at 250 nm which is approximately 1.8-fold greater than the negative band at 245 nm in d-TpT.

Interaction of Dideoxyadenosine Methyl Phosphonates with Poly (U) and Poly (dT)

Figure 14:
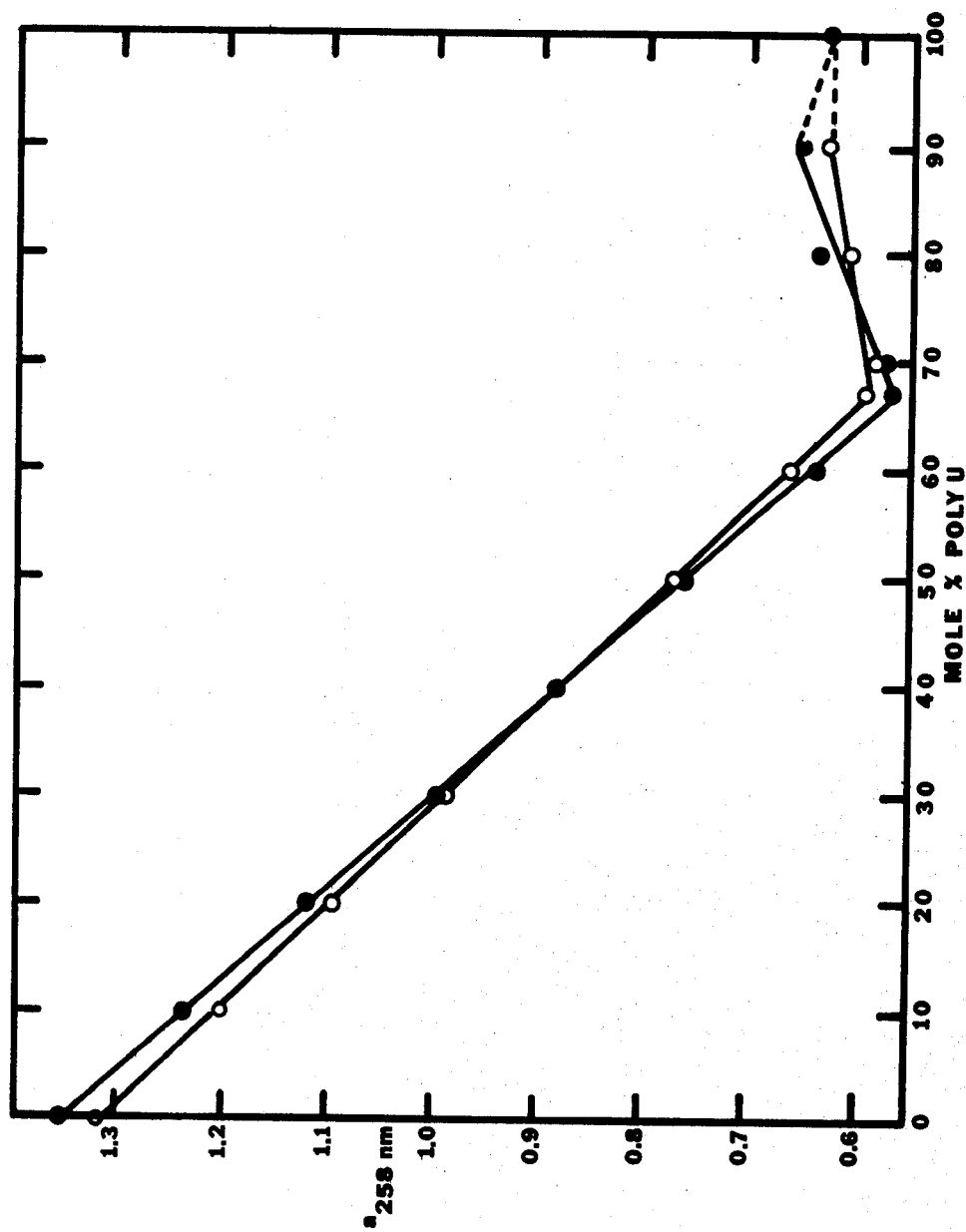
FIG. 14 is a sketch showing mixing experiment between polyuridylic acid and dApA)$_1$ (O) or dApA)$_2$ (o) in 10 mM Tris, 10 mM MgCl$_2$, pH 7.5 at 0° C., with the total nucleotide concentration is $1 \times 10^{-4}$M.

Both diastereoisomers of d-ApA form complexes with poly U at 0° C. The mixing curves for d-ApA₁ and d-ApA)₂ with poly U (FIG. 14) show that complex formation occurs with a base stoichiometry of 2U:1A. Similar results were obtained for the interaction of d-ApAp)₁ and d-ApAp)₂ with poly U and for the interaction of d-ApA with poly (dT).

Figure 15:
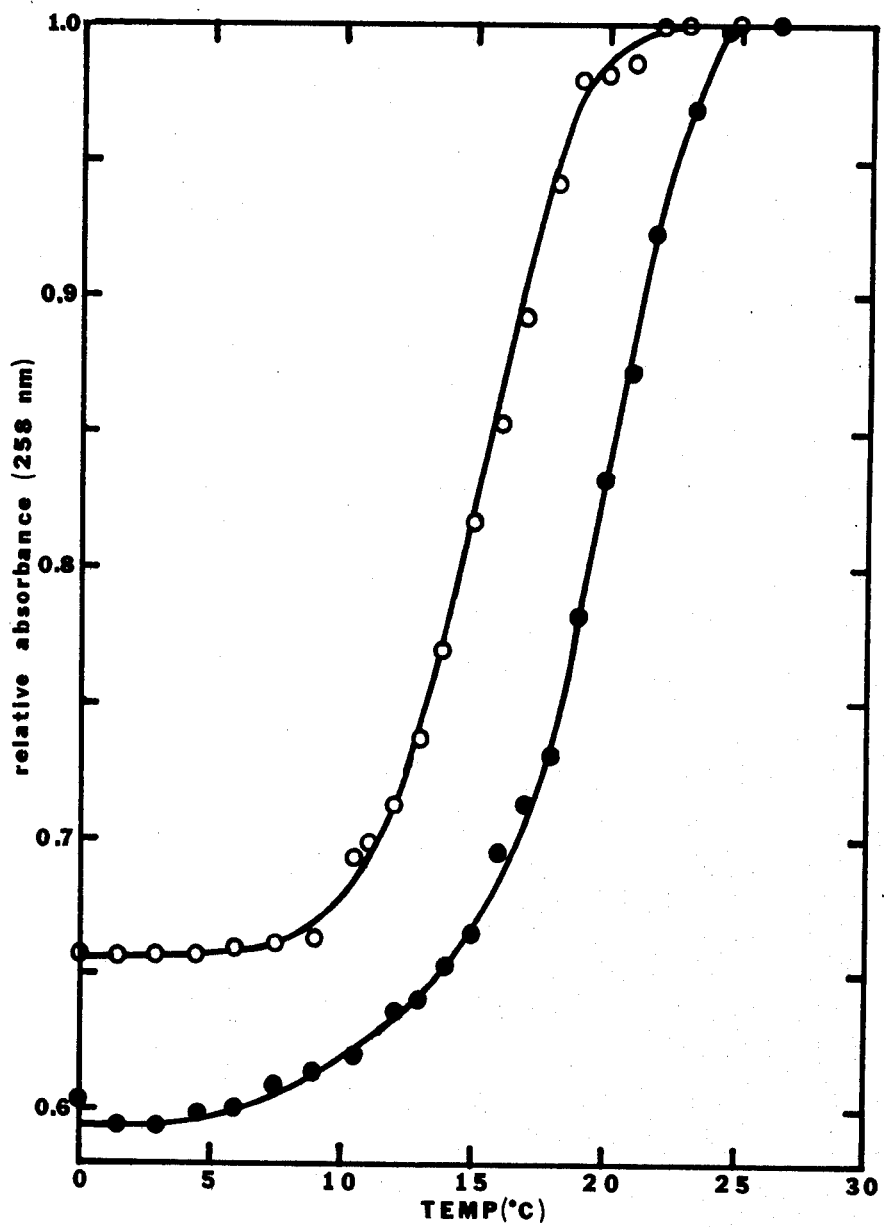
FIG. 15 is a sketch showing melting curves of poly U+dApA)$_1$ (O) and poly U+dApA)$_2$ (o) in 10 mM Tris, 10 mM MgCl$_2$, pH 7.5, with the stoichiometry of each complex is 2U:1A and the total nucleotide concentration is $5 \times 10^{-5}$M.

As shown in FIG. 15, the methyl phosphonate-polynucleotide complexes exhibit a cooperative thermal transition with a well-defined melting temperature. The melting temperature of the d-ApA)₁-poly U complex is 4.4° higher than the d-ApA)₂-poly U complex. A similar difference in melting temperatures for the d-ApAp-poly U complexes was also observed (Table 5). Essentially no difference is observed between the Tm values of the two d-ApA-poly(dT) complexes, however.

Significant increases are observed in the thermal stabilities of the dinucleoside methyl phosphonate-polynucleotide complexes as compared to similar complexes formed between d-ApA and poly U or poly dT. The non-ionic d-Apa forms complexes with Tm values 8.4° and 12.4° higher that that of d-Apa-poly U, while the singly-charged d-ApAp from complexes with Tm values 6.5° and 10.4° higher than d-Apa-poly U. Similarly, the complexes formed between d-ApA and poly (dT) each melt approximately 10° higher than the d-ApA-poly(dt) complex.

TABLE 5

Melting Temperatures of Complexes Formed Between Dideoxyadenosine Methyl Phosphonate Analogs and Polyuridylic Acid or Polythymidylic Acid

| Complex[a] | Tm °C. (poly U)[b] | Tm °C. (poly dT) |
|---|---|---|
| d-ApA | 7.0 | 9.2 |
| (d-ApA)₁ | 15.4 | 18.7 |
| (d-ApA)₂ | 19.8 | 18.4 |
| (d-ApAp)₁ | 13.5 | — |
| (d-ApAp)₂ | 17.4 | — |

[a]Complex stoichiometry: 2U:1A or 2T:1A
[b]10 mM Tris.HCl
10 mM MgCl₂
pH 7.5

Discussion

Dinucleoside methyl phosphonates are novel nucleic acid analogs in which the phosphodiester internucleoside linkage is replaced by a 3'-5' linked internucleoside methyl phosphonyl group. Unlike the dinucleoside methylene phosphonates prepared by others, the methyl phosphonate analogs do not contain a negatively charged backbone and are nonionic molecules at pH 7. The methyl phosphonate group is isosteric with respect to the phosphate group of dinucleoside monophosphates. Thus, these analogs should present minimal steric restrictions to interaction with complementary polynucleotides or single-stranded regions of nucleic acid molecules. Since the methyl phosphonyl group is not found in naturally occuring nucleic acid molecules, this internucleoside linkage may be resistant to hydrolysis by various nuclease and esterase activities and this has in fact been observed (Miller, unpublished data). These properties make analogs of this type potentially useful as vehicles for exploring the interactions of selected oligonucleotide sequences with nucleic acids and nucleic acid-related enzymes within the living cell (Miller et al., 1977).

Figure 17:
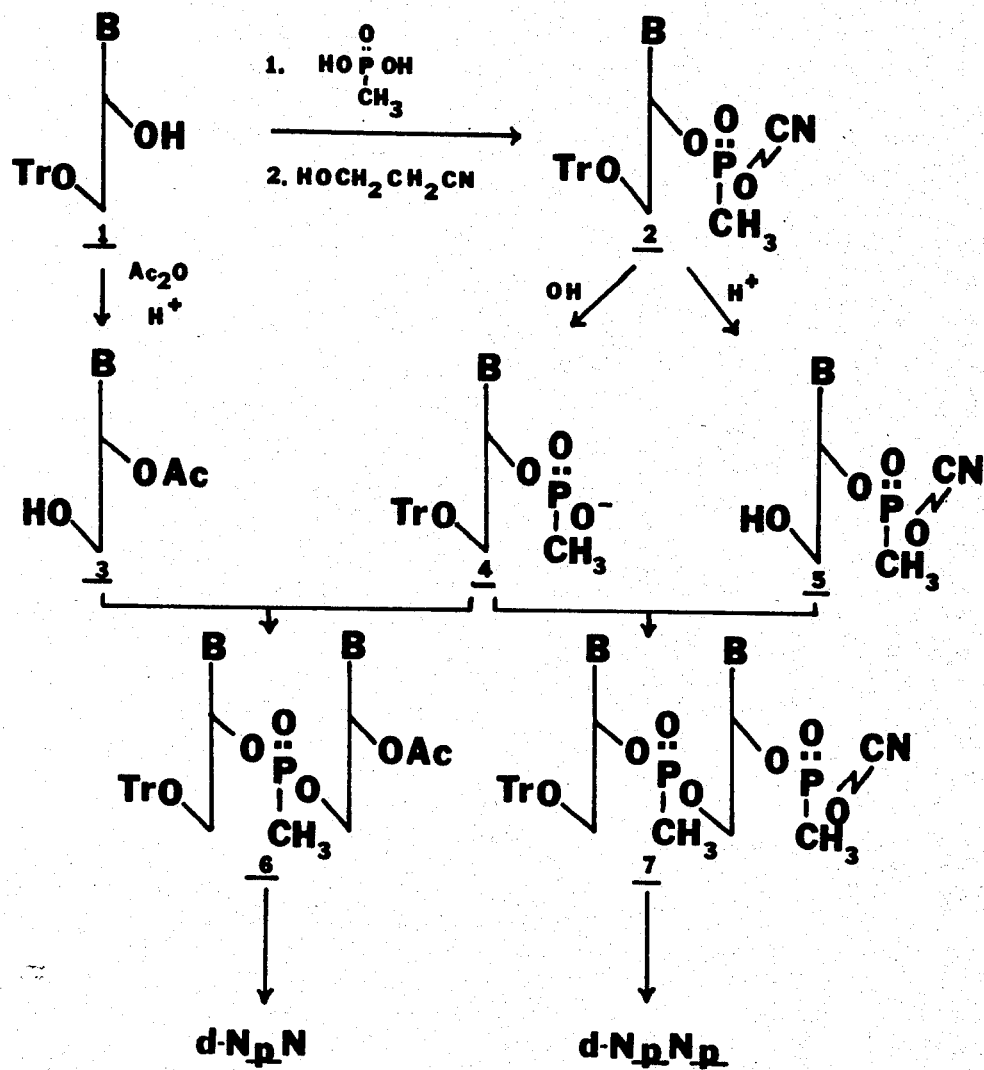
FIG. 17 is a schematic of a synthetic of this invention for preparation of the oligonucleoside methyl phosphonate.

The preparation of the oligonucleoside methyl phosphonates follows the basic strategy used for the preparation of protected oligonucleotide phosphotriesters. The synthetic scheme which has been adopted first involves preparation of a protected nucleoside 3'-methyl phosphonate β-cyanoethyl ester (FIG. 17). This two-step preparation can be carried out in a one-flask reaction and proceeds in high overall yield. Since the product is readily purified by silica gel column chromatography, multigram quantities of this key intermediate can be prepared. By selective removal of the 5'-trityl group or the β-cyanoethyl group, chain extension can proceed in either direction. Thus, compound 2 in FIG. 17 serves as a basic building block for the preparation of longer oligomers. This type of synthetic scheme was originally developed by others for the preparation of oligonucloetide βββ-trichloroethyl phosphotriesters and has more recently been used by others for the preparation of oligonucleotide p-chlorophenyl phosphotriesters. This procedure also allows the preparation of specifically [¹³C]enriched dimers by use of [¹³C]-methyl phosphonic acid in the synthesis of 1. Dimers and oligomers containing [¹³C]-methyl phosphonate groups could be very useful for probing the physical and biological properties of oligonucleoside methyl phosphonates by nuclear magnetic resonance spectroscopic techniques (Cheng et al., manuscript in preparation).

In the present study (FIG. 17), the -cyanoethyl group was removed from 1 and chain extension was continued in the 3'-direction. Two types of condensation reactions were carried out: (1) condensation with a 3'-O-acetylated nucleoside to give dimers with the general structure 6 and (2) condensation with a -ucleoside 3'-methyl phosphonate β-cyanoethyl ester to give dimers with general structure 7. The latter type of dimer can be further extended by removal of the β-cyanoethyl group followed by condensation with other oligonucleoside methyl phosphonate blocks. In this way, oligonucleoside methyl phosphonates containing up to four deoxyadenosine residues and up to nine thymidine residues have been prepared.

Different condensing agents were used in these reactions, including dicyclohexylcarbodiimide (DCC), triisopropylbenzenesulfonyl chloride (TPSCl) and mesitylenesulfonyl tetrazolide (MST). The order of condensing efficiency was found to be MST>TPSCl>DCC. Although DCC did bring about condensation, several days at elevated temperatures were required and the yields were quite low. Considerable improvement in reaction yield was obtained when TPSCl was used. However, again prolonged reaction periods were required and noticeable buildup of side products was observed. The reagent of choice for these reactions in MST. The reaction occurs within a period of several hours, with little or no side products. The efficiency of a particular condensing agent depends not only upon its structure but also upon the nature of the phosphorous-containing substituent which is activated. Thus, when MST was used as a condensing agent, we observed that reactions involving nucleoside 3'-methyl phosphonates or nucleoside 3'-ethyl phosphates usually proceed in lower yield than those involving nucleoside 3'-p-chlorophenyl phosphates.

Figure 16:
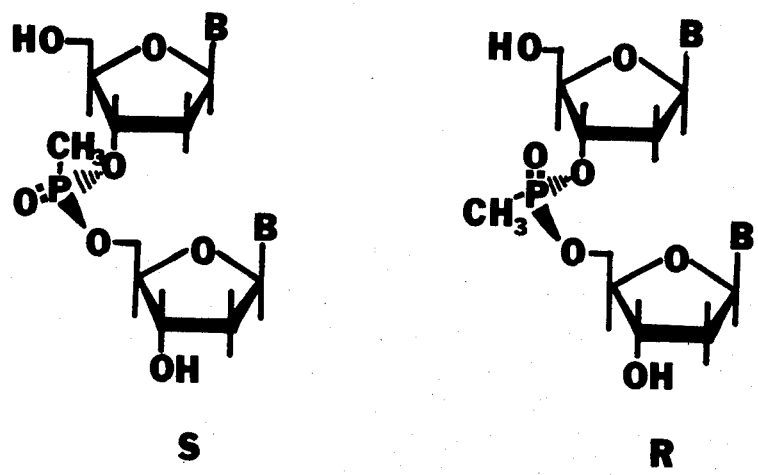
FIG. 16 is molecular diagrams of the diastereoisomers of dideoxyribonucleoside methyl phosphonates.

The ability to separate the individual diastereoisomers of each dimer sequence allowed examination of effect of the configuration of the phosphonyl methyl group on the overall dimer conformation. As shown in FIG. 16, the isomers differ in configuration at the internucleoside linkage with the methyl group assuming either a pseudo-axial or pseudoequitorial position when the dimers are drawn in a stacked conformation. The unique conformational properties of each diastereoisomer of d-ApA and d-ApAp are most readily seen by examining the percent hypochromicity of each diastereoisomer (Table 4). Isomer 1 of both d-ApA and d-ApAp exhibits a greater percent hypochromicity than does isomer 2 of this series. Since the percent hypochromicity is related to the extent of base-base overlap in dimers of this type (Ts'o, 1974), the result suggests that d-ApA)$_1$ and d-ApAp)$_1$ and more highly stacked in solution than are d-ApA)$_2$ and d-ApAp)$_2$. Comparison of the percent hypochromicities of the methyl phosphonate dimers with that of d-ApA shows that these dimers are less stacked than the parent dinucleoside monophosphate. A similar result was observed for the methyl and ethyl phosphotriesters of d-ApA. Thus, non-ionic methyl or ethyl phosphotriester or methyl phosphonate internucleoside linkages appear to perturb the stacking interactions between the bases in these dimers.

The circular dichroism spectra of dinucleoside monophosphates are indicators of both the extent and mode of base stacking, as well as the population of right-handed versus left-handed stacks. The CD spectra of each diastereoisomer for the methyl phosphonate dimer sequences d-ApA, d-ApAp, d-ApT and d-TpA suggest that each diastereoisomer has an unique stacking mode in solution. The profiles of the CD spectra of d-ApA)$_1$ and d-ApAp)$_1$ are very similar to those of d-Apa and r-ApA, and differ only in the magnitude of the molecular ellipticity. This result and the results of the hypochromicity measurements suggest that the stacking modes of the bases in these dimers are similar to those of d-ApA and r-ApA. On the other hand, the profiles of the DC spectra of d-ApA)$_2$ and d-ApAp)$_2$ are quite different. The magnitudes of the molecular ellipticities of dApA)$_2$ and dApAp)$_2$ are greatly diminished, with complete loss of [θ] at 270 nm. Since the hypochromicity measurements suggest that the bases in these dimers have substantial overlap, the mode of stacking in these dimers must be quite different from that found for isomer 1 or for d-ApA. The magnitude of the molecular ellipticity in dimers of this type is sensitive to the angle, θ, between the transition dipoles of the bases. The value of the molecular ellipticity is greatest when θ is 45° and diminishes to 0 when θ is 0°, 90° or 180°. Thus, the most reasonable interpretation of the CD results is that in d-ApA)$_1$ and d-ApAp)$_1$, the bases tend to orient in an oblique manner, while in d-ApA)$_2$ and d-ApAp)$_2$, the bases tend to orient in a parallel or perpendicular manner. This interpretation is supported by the base-base stacking patterns as determined by pmr spectroscopy. The substantial change in the CD profile of d-ApA)$_2$ rather than a simple diminution of the amplitude of the [θ] values suggests that variation of the population of right-handed versus left-handed stacks would not provide an adequate explanation of the CD results.

The CD spectra of d-ApT isomers 1 and 2 have the same shape as the CD spectrum of d-ApT, but with diminished molecular ellipticity. For d-TpA, the spectrum of isomer 2 is identical to that of d-TpAp, while the spectrum of isomer 1 shows diminished [θ] values of the peak and trough regions. Thus, the stacking modes in these methyl phosphonate dimers are expected to be basically similar to the stacking modes of the parent dinucleoside monophosphates, but with perhaps different degrees of base-base overlap or different populations of right- and left-handed stacks.

The dimer, d-ApA, forms stable complexes with both polyribo- and polydeoxyribonucleotides. These poly U and poly dT complexes have greater stability than similar complexes formed by the parent dinucleoside monophosphate, d-ApA. Similar observations have previously been made for triple helix formation between the alkyl phosphotriesters d-Ap(Me)A or d-Ap(Et)A and poly U, for duplex formation between oligonucleotide triesters and tRNA and for helical duplex formation between the octathymidylate ethyl phosphotriester, d-[Tp(Et)]$_7$T, and poly dA. It should be noted, however, that d-[Tp(Et)]$_7$T, in contrast to d-ApA, exhibits selective binding to polydeoxyribonucleotides versus polyribonucleotides in duplex formation.

Previous analyses indicate that the increased stability of the complexes formed between nonionic oligomers and complementary polynucleotides results from the reduction in charge repulsion between the nonionic backbone of the oligomer and the negatively charged sugar-phosphate backbone of the polynucleotide. Although both d-ApAp and d-ApA possess a formal negative charge, the d-ApAp.poly U complexes are more stable than the d-ApA.poly U complex. The 3'-terminal methyl phosphonate group of dApAp is free to rotate away from the negatively charged phosphate backbone of poly U without disrupting the base-pairing and base-stacking interactions in the complex. In contrast, repulsion between the negative charge of the phosphodiester linkage in d-ApA and the polymer backbone directly opposes base-pairing and stacking. Thus, the presence of a negative charge at the internucleotide linkage contributes much more effectively to the charge repulsion effect between the dimers and polynucleotides.

Under the conditions of the present experiments, the Tm values of d-Ap(Me)A.poly U and d-Ap(Et)A.poly U are 13° C. and 12° C. respectively. These Tm values are lower than those of d-ApA and d-ApAp complexes with poly U. These results suggest that the increasing size of the methyl and ethyl side chains in the phosphotriester dimers may provide a greater steric hindrance to complex formation. The methyl group of the phosphonate dimers should be only slightly larger in size than the oxygen of the phosphate group, and thus would be expected to have the least steric effect. A similar phenonenon has been observed when the stabilities of poly U complexes with the ethyl phosphotriester and methyl phosphonate analogs of d-ApApApA are compared.

The differences in the conformations of the individual diastereoisomers of d-ApA and d-ApAp are reflected in their interactions with poly U. For each dimer, the diastereoisomer with greater base-base overlap (isomer 1) forms a complex of lower stability with poly U. In a previous analysis of the influence of C-2' substituents of adenine polynucleotides on the Tm values of the helices, it can be reasoned that the conformation free-energy difference ($F_D$-$F_S$) at the melting temperature is directly related to the Tm value, where $F_D$ represents the free energy of the double-stranded duplex, and $F_S$ represents the free energy of the base-stacked single strand. The values of $F_D$-$F_S$ reflect the conformation of the duplex state and the single-stranded state. The data indicates that ($F_D$-$F_S$) for isomer 1 of dApA or dApAp is slighty less than ($F_D$-$F_S$) for isomer 2 of dApA or dApAp. This reduction may reflect a higher $F_S$ value of isomer 1 since this isomer indeed has a greater degree of stacking, assuming that $F_D$ for isomer 1 and isomer 2 remains the same. In contrast to the behavior with poly U, both diastereoisomers of d-ApA form complexes with poly(dT) which have similar Tm values. Since the geometry of the triple helix of dApA.2 poly U is likely to be different than the geometry of the dApA.2 poly dT triple helix, the difference in $F_S$ of isomer 1 versus $F_S$ of isomer 2 may be compensated by a difference in $F_D$ of isomer 1 versus $F_D$ of isomer 2.

The studies reported here have shown that dideoxyribonucleotide analogs containing nonionic 3'-5' internucleoside methyl phosphonate linkages can be readily synthesized. The configuration of the methyl group in the backbone of these dimers influences their conformation in solution and their ability to form complexes with complementary polyribonucleotides.

In addition, preliminary studies have shown that oligodeoxyribonucleoside methyl phosphonates are resistant to nuclease hydrolysis, are taken up in intack form by mammalian cells in culture and can exert specific inhibitory effects on cellular DNA and protein synthesis. Unlike 2'-O-methyl oligonucleotide ethyl phosphotriesters, the methyl phosphonates appear to have relatively long half-lives within the cells. Thus, oligonucleoside methyl phosphonates of specific sequence could complement oligonucleotide phosphotriesters as probes and regulators of nucleic acid function within living cells.

Nonionic Nucleic Acid Alkyl and Aryl Methylphosphonates

There will now be described the synthesis of a series of oligonucleoside methylphosphonates whose base sequences are complementary to the anticodon loops of tRNA$^{lys}$ and to the —ACCAOH amino acid accepting stem of tRNA. The effects of these analogues on cell-free aminoacylation and cell-free protein synthesis will be considered. The uptake of selected analogues by mammalian cells in culture and the effects of these compounds in bacterial and mammalian cell growth are also discussed.

Materials

Nucleosides were checked for purity by paper chromatography before use. N-Benzoyldeoxyadenosine, N-isobutyryldeoxyguanosine, their 5'-O-dimethoxytrityl derivatives and 5'-O-monomethoxytrityl thymidine were prepared according to published procedures. d-[(Meo)$_2$Tr]bzApbzApCE, d-[(Meo)$_2$Tr]bzApbzAOAC, d-[(Meo)Tr]TpTpCE, d-ApT, d-Ap-[$^3$H]-T, d-TpT and d-Tp-[$^3$H]T were also synthesized by standard procedures.

Dimethylmethylphosphonate and benzenesulfonic acid were used without further purification. Hydracrylonitrite was dried over 4 Å molecular sieves. Methylphosphonic acid dipyridinium salt and mesitylenesulfonyl tetrazolide were prepared.

Anhydrous pyridine was prepared by refluxing reagent grade pyridine (3L) with chlorosulfonic acid (40 ml) for 7 hrs followed by distillation onto sodium hydroxide pellets (40 g). After refluxing for 7 hrs, the pyridine was distilled onto 4 Å molecular sieves and stored in the dark.

Silica gel column chromatography was carried out using Baker 3405 silica gel (60–200 mesh). Thin layer silica gel chromatography (TLC) was performed on E. Merck Silica Gel 60F 254 plastic backed TLC sheets (0.2 mm thick).

High pressure liquid chromatography (HPLC) was carried out using a Laboratory Data Control instrument on columns (2.1 mm×1 m) packed with HC Pellosil. The columns were eluted with a linear gradient (40 ml total) of chloroform to 20% (V/V) methanol in chloroform at a flow rate of 1 ml/min. Ultraviolet spectra were recorded on a Cary 14 or a Varian 219 ultraviolet spectrophotometer with a thermostatted cell compartment.

The following extinction coefficients (260 nm) were used: d-T, 9,100; d-[(Meo)Tr]T, 10,200; d-[(Meo)$_2$Tr]bzA,12,500; d-bzA, 10,600; d-[(Meo)$_2$Tr]ibuG, 17,400; and d-ibuG, 16,700. Paper chromatography was carried out on Whatman 3 mm paper using solvent A: 2-propanol-concentrated ammonium hydroxidewater (7:1:2 V/V).

Preparation of d-[(Meo)$_2$Tr]ibuGpCE:

d-[(Meo)$_2$Tr]ibuG (12 g; 18.7 mmoles) and the pyridinium salt of methyl-phosphonic acid (21 mmoles) were dried by evaporation with anhydrous pyridine (4×20 ml) and the residue in 40 ml of pyridine was treated with 2,4,6-triisopropylbenzenesulfonyl chloride (12.7 g, 42 mmoles) for 8 hrs at room temperature.

Hydracrylonitrile (4.5 g, 63 mmoles) and 2,4,6-triisopropylbenzenesulfonyl chloride (0.61 g, 2 mmoles)

were added and the reaction mixture was kept at room temperature. After 2 days the reaction mixture was poured into 500 ml of ice-cold 5% NaHCO$_3$ solution.

The solution was extracted with ethyl acetate (2×250 ml) and the combined extracts were dried over anhydrous Na$_2$SO$_4$. Examination of the extract by TLC showed the presence of both d-[(Meo)$_2$Tr]ibuGpCE (Rf-0.31 silica gel tlc, 10% MeOH/CHCl$_3$) and d-ibuGpCE (Rf-0.14, silica gel tlc, 10% MeOH/CHCl$_3$).

After concentration, the ethyl acetate extract was chromatographed on silica gel (4×35 cm) using ether (1L) and a 0 to 20% linear gradient of methanol in chloroform (1.6L total) as solvents. d-[(Meo)$_2$Tr]ibuGpCE (2.75 mmoles) was obtained in 15% yield while d-ibuGpCE (2.46 mmoles) was obtained in 13% yield.

Additional d-[(Meo)$_2$Tr]ibuGp (3.69 mmoles, 20%) was obtained from the aqueous bicarbonate solution after extraction with chloroform (2×200 ml).

Preparation of Protected Oligonucleoside Methylphosphonates:

The same general procedures were used for the preparation of dinucleoside methylphosphonates. The specific conditions used in the condensation reactions and the yields obtained after silica gel column chromatography are given in Table VI. The ultraviolet spectroscopic characteristics and the mobilities of the protected oligonucleotides on silica gel TLC and silica gel HPLC are given in Table VII.

Preparation of Oligonucleoside Methylphosphonates:

The protecting groups were removed from the blocked oligonucleoside methylphosphonates using conditions described previously. In the case of the dA-containing oligomers, the N-benzoyl groups were removed by treatment with hydrazine. The oligomers were purified by preparative paper chromatography using solvent A. For the [$^3$H] -labeled oligothymidine methylphosphonates, d-Tp)$_n$-[$^3$H]-T, the condensation reactions containing d-[(Meo)$_2$Tr]Tp)$_n$+[$^3$H]TOAC were run on 0.01 (n=1) and 0.005 (n=4,8) mmole scales while d-GpGp-[$^3$H]-T was prepared on a 0.012 mmole scale.

After completion of the reaction, the protecting groups were removed and the entire reaction mixture was chromatographed on paper. The oligonucleoside methylphosphonates were eluted from the paper with 50% aqueous ethanol. The ethanol solutions were passed through DEAE cellulose columns (0.5×1 cm) and stored at 0° C.

The UV spectral properties and chromatographic mobilities of the oligonucleoside methylphosphonates are given in Table VII. For use in the physical, biochemical, and biological experiments described below, aliquots containing the required amount of oligomer were evaporated to dryness and the oligomer was dissolved in the buffer used in the particular experiment.

TABLE VI

Preparation of Protected Oligodeoxyribonucleoside Methylphosphonates

| 3'-Methylphosphonate Components | (mmoles) | 5'-OH Component | (mmoles) | MST (mmoles) | Product (mmoles) | Yield % |
|---|---|---|---|---|---|---|
| d-[(MeO)$_2$Tr]ibuGp | (0.50) | d-ibuGpCE | (0.50) | 2.0 | d-[(MeO)$_2$Tr]ibuGpibuGpCE (.082) | 16 |
| d-[(MeO)$_2$Tr]ibuGp | (1.0) | d-bzAOAC | (1.5) | 4.0 | d-[(MeO)$_2$Tr]ibuGpbzAOAC (0.42) | 42 |
| d-[(MeO)Tr]TpTp | (0.33) | d-TpTpCE | (0.50) | 1.6 | d-[(MeO)Tr]TpTpTpTpCE (0.168) | 50 |
| d-[(MeO)Tr]Tp(Tp)$_2$TpCE | (0.0324) | d-Tp(Tp)$_2$TpCE | (.0524) | 0.16 | d-[(MeO)Tr]Tp(Tp)$_6$TpCE (.0138) | 43 |
| d-[(MeO)$_2$Tr]ibuGpibuGp | (.07) | d-TOAC | (.15) | 0.28 | d-[(MeO)$_2$Tr]ibuGpibuGpTOAC (0.0153) | 22 |
| d-[(MeO)$_2$Tr]bzApbzAp | (0.065) | d-bzAOAC | (0.043) | 0.163 | d-[(MeO)$_2$Tr]bzApbzApbzAOAC (0.023) | 53 |
| d-[(MeO)$_2$Tr]bzApbzAp | (0.13) | d-bzApbzAOAC | (0.20) | 0.52 | d-[(MeO)$_2$Tr]bzApbzApbzApbzAOAC (0.031) | 24 |
| d-[(MeO)$_2$Tr]bzApbzAp | (0.0168) | d-ibuGpbzAOAC | (0.0168) | 0.0735 | d-[(MeO)$_2$Tr]ApbzApibuGpbzAOAC (0.0029) | 1 |

TABLE VII

Ultraviolet Spectral Properties and Chromatographic Mobilities of Protected Oligodeoxyribonucleoside Methylphosphonates

| Oligomer | λ max. nm | λ min. nm | UV Spectra$^a$ ε$_{260/235}$ calcd. | ε$_{260/235}$ obsvd. | ε$_{260/280}$ calcd. | ε$_{260/280}$ obsvd. | Silica Gel TLC (Rf)$^b$ 5% | 10% | 15% | 20% | Silica Gel HPLC$^c$ Retention time (min) |
|---|---|---|---|---|---|---|---|---|---|---|---|
| d-[(MeO)Tr]TpTpTpTpCE | 265 / 235 sh | 243 | 1.34 | 1.31 | 1.55 | 1.64 | — | — | .08 | .29 | — |
| d-[(MeO)Tr]Tp(Tp)$_6$TpCE | 265 | 243 | 1.75 | 0.92 | 1.57 | 1.56 | — | 0.00 | — | .13 | — |
| d-[(MeO)$_2$Tr]ibuGpibuGpCE | 238 / 253 / 260 / 280 | 225 / 245 / 256 / 270 | 1.19 | 1.05 | 1.33 | 1.32 | — | 0.16 | — | — | 19.2 |
| d-[(MeO)$_2$Tr]ibuGpbzAOAC | 235 / 278 | 256 | 0.82 | 0.75 | 0.88 | 0.87 | — | 0.29 | — | — | 12.3 |
| d-ibuGpbzAOAC | 260 / 280 | 239 / 267 | 1.63 | 1.27 | 0.90 | 0.90 | — | 0.18 / 0.14 | — | — | 15.5 / 17.6 |
| d-[(MeO)$_2$Tr]ibuGpibuGpTOAC | 240 sh / 260 / 275 sh | 228 | 1.34 | 1.51 | 1.38 | 1.45 | — | 0.18 | — | — | 16.0 |
| d-[(MeO)$_2$Tr]bzApbzApbzAOAC | 234 / 280 | 227 / 255 | 0.66 | 0.61 | 0.59 | 0.59 | — | 0.41 / 0.38 | 0.55 / 0.53 | — | 13.4 / 14.3 |
| d-[(MeO)$_2$Tr]bzApbzApbzApbzAOAC | 233 sh / 280 | 253 | 0.71 | 0.60 | 0.59 | 0.60 | — | — | 0.31 | — | 19.3 |
| d-[(MeO)$_2$Tr]bzApbzApibuGpbzAOAC | 235 sh | 255 | 0.89 | 0.74 | 0.73 | 0.75 | — | 0.15 | 0.44 | — | 23.8 |

TABLE VII-continued
Ultraviolet Spectral Properties and Chromatographic Mobilities of Protected Oligodeoxyribonucleoside Methylphosphonates

| Oligomer | UV Spectra[a] | | | | | | Silica Gel TLC (Rf)[b] | | | | Silica Gel HPLC[c] Retention time (min) |
| --- | --- | --- | --- | --- | --- | --- | --- | --- | --- | --- | --- |
| | λ max. nm | λ min. nm | ε260/235 calcd. | obsvd. | ε260/280 calcd. | obsvd. | 5% | 10% | 15% | 20% | |
| | 280 | | | | | | | | | | |

[a]Measured in 95% ETOH
[b]EM silica gel 60 F$_{254}$ sheets, 0.2 mm thick.
[c]HC Pellosil (2.1 mm × 1 m) 0% to 20% methanol in chloroform 1 ml/min., 40 ml total volume

Interaction of Oligodeoxyadenylate Methylphosphonates With Polynucleotides

The continuous variation experiments and melting experiments were carried out. The extinction coefficients of the oligomers were determined by comparing the absorption of a solution of the oligomer in water at pH 7.0 to the absorption of the same solution at pH 1.0. The oligomer extinction coefficient was calculated from the observed hyperchromicity of the oligomer at pH 1.0 by using the following extinction coefficients: d-A pH 1.0, $14.1 \times 10^3$ and d-G pH 1.0, $12.3 \times 10^3$. The molar extinction coefficient of poly(U) is $9.2 \times 10^3$ (265 nm) and of poly(dT) is $8.52 \times 10^3$ (264 nm).

Cell-Free Aminoacylation (1) *E. coli* system: Unfractionated tRNA *E. coli* was purchased from Schwarz Mann and unfractionated *E. coli* aminoacyl synthetase was purchased from Miles Laboratories, Inc. Reactions were run in 60 μl buffer containing 100 nM Tris, HCl, pH 7.4, 10 mM Mg(OAC)$_2$, 5 mM KCl, 2 mM ATP, 4 μM [$^3$H]-amino acid, 1.8 μM tRNA *coli* and 0 to 100 μM oligonucleotide.

Reactions were initiated by addition of 4 μg of aminoacyl synthetase. Aliquots (10 μl) were removed at various times, added to 1 ml of cold 10% trichloroacetic acid and the resulting precipitate filtered on Whatman G/F filters.

After washing with 4 (1 ml) portions of 2N HCl and 4 (1 ml) portions of 95% ETOH, the filters were dried and counted in 7 ml New England Nuclear 949 scintillation mixture.

(2) Rabbit Reticulocyte System

A rabbit reticulocyte cell-free translation system was obtained from New England Nuclear. Reactions were run in 12.5 μl of buffer containing 1 μl translation mixture, 79 mM potassium acetate, 0.6 mM magnesium acetate, 57 μM [$^3$H]-Lysine, and 50 μM oligomer. The reactions were initiated by addition of 5 μl of reticulocyte lysate and were assayed as described for the *E. coli* system.

Cell-Free Protein Synthesis (1) *E. coli* system

A cell-free protein synthesizing system was isolated from *E. coli* B cells (S-30). The system incorporates 300 pmoles of [$^3$H]-phenylalanine/mg of S-30 protein after 15 min incubation at 37° C. when poly U is used as a message.

(2) Rabbit Reticulocyte

The reticulocyte translation system prepared by New England Nuclear was used. For the translation of globin mRNA the reactions were run in 12.5 μl of buffer containing: 1 μl of translation mixture, 0.10 μg of globin mRNA (Miles Laboratories), 79 mM, potassium acetate, 0.2 mM magnesium acetate 0 to 50M oligomer and 20.5 μM [$^3$H]-leucine.

For the translation of poly(U) the reactions were run in 12.5 μl buffer containing: 1 μl of translation mixture, 120 mM potassium acetate, 0.8 mM magnesium acetate, 367 μM poly(U), 0 to 200 μM oligomer (base concentration) and 32 μM [$^3$H]-phenylalanine. Reactions were initiated by addition of 5 μl of reticulocyte lysate.

Aliquots (2 μl) were removed at various times and added to 1.0 ml of bovine serum albumin (100 μg) solution. The protein was precipitated by heating with 1 ml of 10% trichloroacetic acid at 70° C.; filtered on G/F filters and counted in 7 ml of Betaflour.

Uptake of Oligodeoxyribonucleoside Methylphosphonates

The uptake of d-Ap-[$^3$H]-T, d-GpGp-[$^3$H]-T and d-Tp)$_n$-[$^3$H]-T by transformed Syrian hamster fibroblasts were determined.

Effects of Oligodeoxyribonucleoside Methylphosphonates On Colony Formation (1) *E. coli*

*E. coli* B was grown in M-9 medium supplemented with glucose (36 g/l) and 1% Casamino acids. The cells were harvested in midlog phase and resuspended in 50 μl of fresh medium containing 0 to 160 μM oligomer at a final cell density of $1 \times 10^4$ cells/ml.

The cells were incubated for 1 hr. at 37° C. and then diluted with 0.9 ml of medium. A 0.8 ml aliquot was added to 2.5 ml of 0.8% Bactoagar at 45° C. This solution was quickly poured onto a 100 mm plate containing solid 1.2% Bactoagar. After solidification, the plates were incubated overnight at 37° C. and the resulting colonies were counted.

(2) Transformed Syrian Hamster Embryonic Fibroblasts (BP-6) and Transformed Human Fibroblasts (HTB1080)

Colony formation by the fibroblasts in the presence of the methylphosphonate analogues was carried out.

RESULTS

Synthesis of Oligodeoxyribonucleoside Methylphosphonates

The synthetic scheme used for preparing the oligonucleoside methylphosphonates followed the basic approach used to synthesize dideoxyribonucleoside methylphosphonates. Suitably protected monomers or oligomer blocks carrying a 3'-terminal methylphosphonate group were condensed with protected mono- or oligonucleotides bearing a free 5'-hyroxyl group. Mesitylenesulfonyl tetrazolide was used as the condensing agent. The fully protected oligomers were purified by silica gel column chromatography. The reaction conditions used and the yields obtained are given in Table VI. The oligomers were characterized by ultraviolet spectroscopy, thin layer chromatography and high pressure liquid chromatography as indicated in Table VII.

The protecting groups were removed as previously described. In the case of the deoxyadenosine-containing oligomers, the N-benzoyl groups were first removed by treatment with hydrazine hydrate. The remaining 3'-O acetyl and 5'-O dimethoxytrityl groups were removed by sequential treatment with ammonium hydroxide and 80% acetic acid. The oligomers were purified by preparative paper chromatography and were characterized by UV spectroscopy (Table VIII).

Interaction of Oligodeoxyribonucleoside Methylphosphonates With Complementary Polynucleotides Table IX summarizes the melting temperatures of complexes formed between oligodeoxyadenosine methylphosphonates and poly (U) or poly (dT). For comparison, the melting temperatures of complexes formed by oligodeoxyribo- and oligoriboadenosines are included. Each oligomer forms a triple-stranded complex with a stoichoimetry of 2U:1A or 2T:1A.

The melting temperatures increase as the chainlength of the oligonucleotide increases. For a given chain length, the complexes formed by the methylphosphonate analogues melt at higher temperatures than those formed by the natural diester oligomers.

ester, $G^m p$ (Et)-$G^m p$(Et)-[$^3$H]-U, which are: 9,300$M^{-1}$ (0° C.), 1,900$M^{-1}$, (22° C.) and 2,000$M^{-1}$ (37° C.).

Effect of Oligodeoxyribonucleoside Methylphosphonates on Cell-Free Aminoacylation to tRNA The effects of selected oligodeoxyribonucleoside methylphosphonates on aminoacylation of unfractionated tRNA E. coli are shown in Table X. Three amino acids were tested at various temperatures. The deoxyadenosine-containing analogs which are complementary to the —UUUU— sequence of the anticodon of $tRNA_{E.coli}{}^{lys}$ have the largest inhibitory effect on aminoacylation of $tRNA_{E.coli}{}^{lys}$.

The percent inhibition increases with increasing chain length and decreases with increasing temperature. Inhibition by d-ApApGpA and by the diesters dApApApA is less than that exhibited by d-ApApApA. In contrast to their behavior with $TRNA_{E.coli}{}^{lys}$, neither the methylphosphonates, d-ApApApA, d-ApApGpA nor the phosphodiesters, d-ApApApA, r-ApApApA, had any inhibitory effect on $tRNA_{rabbit}{}^{lys}$ in the rabbit reticulocyte cell-free system (data not shown).

TABLE VIII

Spectral Properties and Chromatographic Mobilities of Oligodeoxyribonucleoside Methylphosphonates

| Oligomer | UV Spectra[a] λ max. nm | λ min. nm | $\epsilon_{260}/\epsilon_{280}$ | $\epsilon$ λ max. | Paper Chromatography[b] Rf Solvent A |
|---|---|---|---|---|---|
| d-GpGpT[c] | 257<br>270 sh | 230 | 1.45 | 33.4 × 10³ | 0.31 |
| d-ApApA | 258 | 232 | 4.27 | 39.0 × 10³ | 0.29 |
| d-ApApApA | 258 | 230 | 3.77 | 50.4 × 10³ | 0.11 |
| d-ApApGpA | 258 | 227 | 3.03 | 50.3 × 10³ | 0.11 |
| d-Tp-[³H]—T | 267 | 235 | 1.53 | — | 0.59 |
| (d-Tp)₄-[³H]—T | 266 | 235 | 1.49 | — | 0.21 |
| (d-Tp)₈-[³H]—T | 266 | 235 | 1.56 | — | 0.17 |

[a] Measured in water, pH 7.0
[b] Rf pT = 0.11
[c] The UV spectrum is similar to that of d-GpGpT (Miller et. al., 1974).

TABLE IX

Interaction of Oligonucleoside Methylphosphonates with Complementary Polynucleotides[a]

| Oligomer | Tm Poly U (2U:1A) | Tm Poly dT (2T:1A) |
|---|---|---|
| d-ApA isomer 1 | 15.4 | 18.7 |
| isomer 2 | 19.8 | 18.4 |
| d-ApApA | 33.0 | 36.8 |
| d-ApApApA | 43.0 | 44.5 |
| d-ApA | 7.0 | 9.2 |
| d-ApApApA | 32.0 | 35.5 |
| r-ApApApA | 36.2° C. | 2.4° C. |

[a] 5 × 10⁻⁵ M total [nucleotide], 10 mM Tris, 10 mM MgCl₂, pH 7.5

With the exception of r-ApApApA, the complexes formed by the oligomers with poly (dT) have slightly higher melting temperatures than the corresponding complexes formed with poly (U).

The interaction of d-GpGp-[³H]-T with unfractionated tRNA E.coli was measured by equilibrium dialysis. The apparent association constants at 0°, 22°, and 37° C. are 1,100$M^{-1}$, 200$M^{-1}$, and 100$M^{-1}$ respectively. These binding constants are much lower than those of the 2'-O-methylribooligonucleotide ethyl phosphotri-

TABLE X

Effects of Oligonucleoside Methylphosphonates on Aminoacylation in an E. coli Cell-Free System

| | % Inhibition[b] | | | | |
|---|---|---|---|---|---|
| | Phe | Leu | Lysine | | |
| Oligomer[a] | 0° C. | 0° C. | 0° C. | 22° C. | 37° C. |
| d-ApA | 6 | 0 | 7 | — | — |
| d-ApApA | 9 | 0 | 62 | 15 | 0 |
| d-ApApApA | 9 | 12 | 88 | 40 | 16 |
| d-ApApGpA | 12 | 12 | 35 | 0 | — |
| d-GpGpT | 31 | 5 | 34 | 9 | 15 |
| dGpGpT (400 μM) | 23 | — | — | — | — |
| d-ApApApA | 0 | 7 | 71[c] | 15[c] | — |
| r-ApApApA | — | — | 78[d] | 17[d] | — |

[a] [oligomer] = 50 μM
[b] [tRNA$_{coli}$] = 2 μM
[c] [oligomer] = 100 μM
[d] [oligomer] = 125 μM

Effects of Oligodeoxyribonucleoside Methylphosphonates On Cell-Free Protein Synthesis The ability of deoxyadenosine containing oligonucleoside methylphosphonates to inhibit polypeptide synthesis in cell-free systems directed by synthetic and natural messages was tested. The results of these experiments are given in Table XI. Poly (U) directed phenylalanine incorporation and poly (A) directed lysine incorporation are both inhibited by oligodeoxyadenosine methylphosphonates and diesters in the E.coli system at 22° C. The percent inhibition increases with oligomer chain length and is greater for polyphenylalanine synthesis. The methylphosphonate analogues are more effective inhibitors than either d-ApApApA or r-ApApApA at the same concentration. Although both the oligodeoxyadenosine methylphosphonates and the phosphodiesters inhibit translation of poly (U) in the rabbit reticulocyte system, no effect on the translation of globin message was observed.

As in the case of the E.coli system, inhibition of phenylalanine incorporation increased with oligomer chain length and was greater for the methylphosphonate analogues than for the diesters.

Uptake of Oligodeoxyribonucleoside Methylphosphonates By Mammalian Cells

Figure 18:
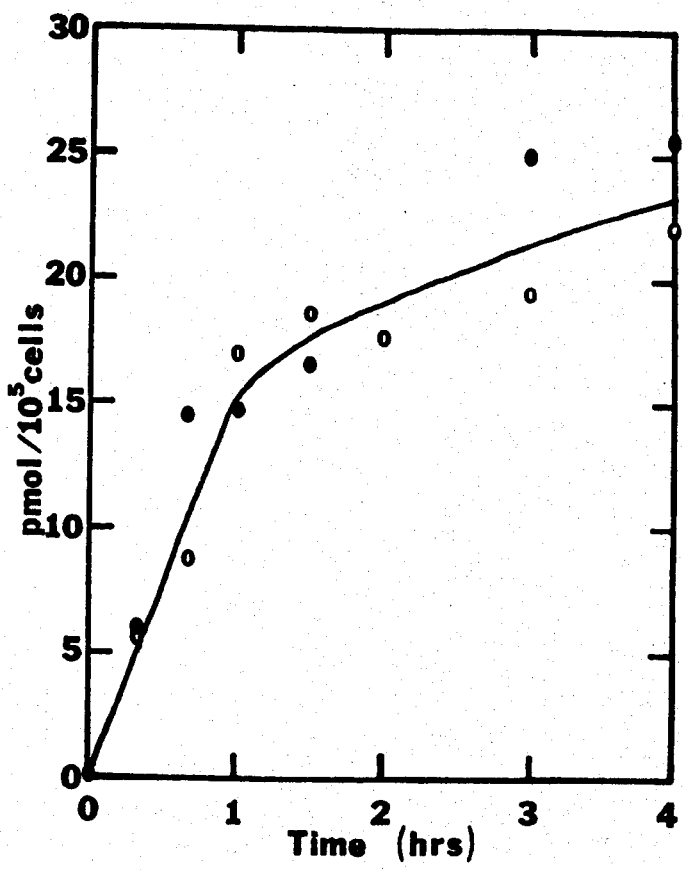
FIG. 18 illustrates the transport of (O) 100 μM d-GpGp-[$^3$H]-T and (o) 100 μM d-Tp)$_8$-[$^3$H]-T into transformed Syrian hamster fibroblasts growing in monolayer at 37° C.

FIG. 18 shows the incorporation of radioactive 100 μM d-GpGp-[$^3$H]-T with time into transformed Syrian hamster embryonic fibroblasts growing in monolayer. The incorporation is approximately linear for the first hour and begins to level off after 1.5 hours. The concentration of radioactivity inside the cell is approximately 117 μM after 1.5 hours assuming a cell volume of 1.5 μl/10$^6$ cells.

TABLE XI
Effects of Oligonucleoside Methylphosphonates on Bacterial and Mammalian Cell-Free Protein Synthesis at 22° C.

| | E. coli | | Rabbit Reticulocyte | |
|---|---|---|---|---|
| Oligomer | Poly U directed[a] | Poly A directed[b] | Poly U directed[a] | Globin mRNA directed[c] |
| d-ApA | 20 | 10 | — | — |
| d-ApApA | 84 | 30 | 81 | — |
| d-ApApApA | 100 | 65 | 77 | 0 |
| d-ApApGpA | 22 | — | — | 0 |
| d-ApApApA | 13 | 19 | 18 | 0 |
| r-ApApApA | 18 | 17 | 85 | 0 |

[a][Poly U] = 360 μM in U
[oligomer] = 175–200 μM in base
[b][Poly A] = 300 μM in A
[oligomer] = 175–200 μM in base
[c][oligomer] = 200 μM in base Cells were incubated with 25 μM d-GpGp-[$^3$H]-T for 18 hours. The medium was removed, the cells were washed with phosphate buffer and then lysed with SDS. Approximately 30% of the total radioactivity from the lysate was found in TCA precipitable material. The DNA was precipitated from the lysate and digested with deoxyribonuclease and snake venom phosphodiesterade. The culture medium, the DNA-free lysate and the DNA digest were each examined by paper chromatography. Only intact d-GpGp-[$^3$H]-T was found in the medium. Radioactivity corresponding to [$^3$H]-TTP (6%) and to d-GpGp-[$^3$H]-T (94%) was found in the lysate, while the DNA digest gave [$^3$H]-dpT and [$^3$H]-dT as products.

Similar uptake studies were carried out with d-Ap[$^3$H]-T and with a series of oligothymidylate analogues, d-(Tp)n-[$^3$H]-T (n=1,4,8). The rates and extents of uptake of these analogues were very similar to that of d-GpGp-[$^3$H]-T (FIG. 1). Examination of the culture medium and cell lysate after overnight incubation with these oligonucleotides gave results similar to those found for d-GpGp-[$^3$H]-T.

Effects of Oligodeoxyribonucleoside Methylphosphonates On Colony Formation By Bacterial and Mammalian Cells The effects of selected oligodeoxyribonucleoside methylphosphonates on colony formation of E. coli B, transformed Syrian hamster fibroblast (BP-6) and transformed human fibroblast (HTB 1080) cells are summarized in Table XII. The d-Ap)nA analogues appear to inhibit E. coli colony formation at high concentrations (160 μM). However, no inhibitory effects on cellular protein or DNA synthesis could be detected in the presence of these compounds by the present assay procedures.

TABLE XII
Effects of Oligonucleoside Methylphosphonates on Colony Formation by Bacterial and Mammalian Cells in Culture

| | % Inhibition[a] | | | |
|---|---|---|---|---|
| | E. coli B | | | HTB 1080 |
| Oligomer | 50 μM | 160 μM | BP-6 (50 μM) | (50 μM) |
| d-ApT | 4 | 5 | 5, 16[b] | 12 |
| d-ApA | 8 | 58 | 6, <1[b] | 5 |
| d-ApApA | 3 | 44 | 29 | 31 |
| d-ApApApA | 19 | 78 | 36 | 19 |
| d-GpGpT | 7 | 11 | 7 | 9 |

[a]The results are the average of two or three experiments. Each experiment consisted of 2 plates (bacterial cells) or 3 plates (Mammalian cells). The average variation is: ±3% in % inhibition. The cells were treated with and grown in the presence of the oligomer at 37° C.
[b]The % inhibition of isomer 1 and 2 respectively.

Colony formation of both transformed hamster and human cells are inhibited to various extents by the oligonucleoside methylphosphonates. Both the hamster and human cells appear to be affected to a similar extent by a given analogue. It appears in the case of dApA, that each diastereoisomer exerts a different inhibitory effect on the growth of the hamster cells. As in the case of E. coli, no inhibition of cellular protein synthesis could be detected.

DISCUSSION

Oligodeoxyribonucleoside methylphosphonates with sequences complementary to the anticodon loop of tRNA$^{lys}$ and to the —ACCA—OH amino acid accepting stem of tRNA were prepared in a manner similar to that used to prepare dideoxyribonucleoside methylphosphonates.

The present studies demonstrate the ability to join blocks of protected methyl-phosphonates to give oligomers with chain lengths up to nine nucleotidyl units. The yields in these condensation reactions are acceptable, although reactions involving deoxyguanosine residues appear to proceed in low yield.

Similar difficulties have been encountered in the syntheses of oligonucleotide phosphotriesters. Unlike the dideoxyribonucleoside methyl-phosphonates previously reported, the oligodeoxyribonucleoside methylphosphonates prepared for this study were not resolved into their individual diastereoisomers.

The oligodeoxyadenosine analogues form triple stranded complexes with both poly(U) and poly(dT). These complexes are more stable than similar complexes formed by either oligoribo- or oligodeoxyribonucleotides. As previously suggested for oligonucleotide ethyl phosphotriesters, and dideoxyribonucleoside methyl-phosphonates, this increased stability is attributed to the decreased charge repulsion between the nonionic backbone of the analogue and the negatively charged complementary polynucleotide backbone. With the exception of r-ApApApA (Table IX), the stability of the complexes formed with poly (dT) are slightly higher than those formed with poly(U), a situation which is also observed for the interaction of poly(dA) with poly(dT) and with poly(U). The lower stability of the (r-ApApApA).2 poly(dT) complex is also reflected at the polymer level.

T..us, under the conditions of the experiments described in Table IX, it was found that the Tm of poly(-rA).2 poly(rU) is 83° C. while the Tm of poly(rA).2 poly(dT) is 59° C. It was observed that formation of the poly(rA).2 poly(dT) complex occurs only at a sodium ion concentration of 2.5M in the absence of magnesium, while poly(rA).2 poly(rU) forms in 0.1M sodium phosphate buffer.

The oligodeoxyadenosine methylphosphonates and their parent dieters selectively inhibit cell-free aminoacylation of tRNA$_{E.coli}^{lys}$. The extent of inhibition is temperature dependent and parallels the ability of the oligomers to bind to poly(U). These observations and the previously demonstrated interaction or r-ApApApA with tRNA$_{E.coli}^{lys}$ suggest that inhibition occurs as a result of oligomer binding to the —UU-UU— anticodon loop of the tRNA. The reduced inhibition observed with d-ApApGpA is consistent with this explanation, since interaction of this oligomer with the anticodon loop would involve formation of a less stable G.U base pair.

Recent studies by others have shown that the rate of aminoacylation of tRNA$_{E.col}^{lys}$ substituted with 5-fluorouracil is considerably lower than that of non-substituted tRNA$_{E.coli}^{lys}$. The increased Km of the 5-fluorouracil substituted tRNA suggested a decreased interaction with the lysyl aminoacyl synthetase.

These results and those of others suggest that the anticodon loop of tRNA$_{E.coli}^{lys}$ is part of the synthetase recognition site. Thus, inhibition of aminoacylation by the oligodeoxyribonucleoside methylphosphonates could result from the reduction in the affinity of the synthetase for tRNA$^{lys}$-oligonucleotide complexes.

The greater inhibition observed with d-ApApApA versus the diesters, d-ApApApA or r-ApApApA may result from greater binding of the analogue to the anticodon loop or to the decreased ability of the synthetase to displace the nonionic oligonucleotide analogue from the anticodon loop.

Alternatively, oligomer binding to the anticodon loop could induce a conformational change in the tRNA, leading to a lower rate and extent of aminoacylation. Such conformational changes have been detected when r-ApApApA binds to tRNA$_{E.coli}^{lys}$.

None of the oligomers have any effect on the aminoacylation of tRNA$_{rabbit}^{lys}$ in a cell free system. Since the anticodon regions of tRNAs from bacterial and mammalian sources probably are similar, the oligo A analogues are expected to interact with the anticodon region of both tRNA$^{lys}$s. The failure to observe inhibition of aminoacylation of tRNA$_{rabbit}^{lys}$ in the presence of these oligo d-A analogs suggestes that there may be a difference between the interaction of the lysine aminoacyl synthetase with tRNA$^{lys}$ from E. coli and from rabbit systems, or a difference between the structure of these two tRNA$^{lys}$s in response to the binding of oligo A analogues.

The trimer, dGpGpT, inhibits both phenylalanine and lysine aminoacylation at 0°, but has little effect on leucine aminoacylation. The aminoacyl stems of both tRNA$_{E.coli}^{lys}$; and tRNA$_{E.coli}^{Phe}$ terminate in a G-C base pair between nucleotides 1 and 72, while a less stable G-U base pair is found at this position in tRNA$_{E.coli}^{leu}$. Thus the observed differences in inhibition of aminoacylation by d-GpGpT may reflect differences in the ability of this oligomer to bind to the different —ACC— ends of the various tRNAs.

Inhibition of lysine aminoacylation by dGpGpT is very temperature sensitive and parallels the decrease in binding to tRNA with increasing temperature. This behavior of d-GpGpT contrasts that of G$_p{}^m$(ET)G$_p{}^m$(ET)U. Although both oligomers can potentially interact with the same sequences in tRNA, the 2'-O-methylribotrinucleotide ethyl phosphotriester binds more strongly and more effectively inhibits aminoacylation. The differences in binding ability may be due to overall differences in the conformation of the deoxyribo- versus 2'-O-methylribo backbones of these oligomers.

The oligodeoxyribonucleoside methylphosphonates effectively inhibit polyphenylalanine synthesis in cell-free systems derived from both E. coli and rabbit reticulocytes. In the E. coli system, the extent of inhibition by the oligodeoxyadenosine analogures parallels the Tm values of the oligomers wiht poly(U), The tetramer, d-ApApGpA which would have to form a G.U base pair with polyU, was 4.5-fold less effective than d-ApApApA.

These results suggests that the oligomers inhibit polypeptide synthesis as a consequence of forming complexes with the poly(U) message. A similar inhibitory effect by poly(dA) on the translation of poly(U) has been observed by others.

It is unlikely that inhibition results from non-specific interaction of the methylphosphonates with protein components of the translation systems.

In the E. coli system, poly(A) translation is inhibited to a lesser extent than is translation of poly(U), while in the reticulocyte system, no inhibition of globin mRNA translation is observed.

The data suggest that the magnitude of inhibition of poly(U)-directed polypeptide synthesis in the E. coli system does not reflect proportionally the ability of the oligomer to bind to poly(U). Although the oligomer pairs d-ApApA/d-ApApApA and d-ApApApA/r-ApApApA form complexes with poly(U) which have very similar Tm's (see Table IX), in each case the methylphosphonate analogues inhibit 5.5 to 6.5 times better than do the diesters. The stronger inhibitory effect could result from a decreased ability of the ribosome to displace the nonionic oligodeoxyribonucleoside methylphosphonates form the poly(U) message, or alternatively, there may be a degradation of the oligonucleotides (phosphodiesters) by nucleases in the cellfree translation systems, but not the corresponding phosphonate analogues.

Experiments with radioactively labeled oligonucleotide methylphosphonates show that these analogues are taken up by mammalian cells growing in culture. The extent of uptake is consistent with passive diffusion of the oligomer across the cell membrane. Both d-Tp-[$^3$H]-T and d-(Tp)$_8$-[$^3$H]-T are taken up to approximately the same extent which suggests that there is no size restriction to uptake over this chain length range. This behavior is in contrast to results obtained with E. coli cells.

Examination of lysates of mammalian cells exposed to labeled oligomers for 18 hours showed that approximately 70% of the labeled thymidine was associated with intact oligomer with the remainder found in thymidine triphosphate and in cellular DNA.

These observations indicate that the oligodeoxyribonucleoside methylphosphonates, which are recovered intact from the culture medium, are slowly degraded within the cell. Failure to observe shorter oligonucleotides and the known resistance of the methylphosphonate linkage to nuclease hydrolysis suggests that degradation may result from cleavage of the 3'-terminal [³H]-thymidine N-glycosyl bond with subsequent reutilization of the thymine base.

The uptake process of the oligonucleoside methylphosphonates is quite different from that of previously studied oligonucleotide ethyl phosphotriesters.

In the case of G$_p$$^m$(Et)G$_p$$^m$(Et)-[³H]-U, the oligomer is rapidly taken up by the cells and is subsequently deethylated. Further degradation to smaller oligomers is then observed, presumably as a result of nuclease-catalyzed hydrolysis of the resulting phosphodiester linkages.

Approximately 80% of the oligomer is metabolized within 24 hours. Although the rate of uptake of d-Gp(Et) Gp(ET)-[³H]-T is similar to that of d-GpGp-[³H]-T, examination of the cell lysate showed extensive degradation of the phosphotriester analogue. The relatively long half lives of the oligodeoxyribonucleoside methylphosphonates may be of value in potential pharmacological applications of these oligonucleotide analogues.

The effects of these analogues on cell colony formation confirmed that the methylphosphonates are taken up by both mammalian and bacterial cells. All the oligomers tested inhibited colony formation of both cell types of various extents. The mechanism(s) by which these compounds exert their inhibitory effects is currently under investigation.

No decrease in either overall short term cellular protein synthesis or DNA synthesis was detected by the present procedure in the presence of these compounds. This does not rule out the possibility that the syntheses of certain critical proteins are perturbed by these oligomers. Currently, studies are being made of this possibility by examination of the cellular proteins using 2-dimensional gel electrophoresis.

The experiments described hereinbefore extend these studies on the use of nonionic oligonucleotides as sequence/function probles of nucleic acids both in biochemical experiments and in living cells. In a future, there will be described the effects of an oligodeoxyribonucleoside methylphosphonate complementary to the 3'-terminus of 16S rRNA on bacterial protein synthesis and growth. The results here, however, suggest that sequence specific oligonucleoside methylphosphonates may find important applications in probing and regulating nucleic acid function within living cells.

What is claimed is:

1. Alkyl or aryl phosphonate nucleic acid analogs, comprising, at least five nucleosides, and an alkyl or aryl phosphonate group, said nucleosides being linked together by said alkyl or aryl phosphonate group to form phosphonate nucleic acid analogs, where the alkyl phosphonate group or the aryl phosphonate group do not sterically hinder the phosphonate linkage or interact with each other, said alkyl or aryl phosphonate nucleic acid analog as defined by the structural formula:

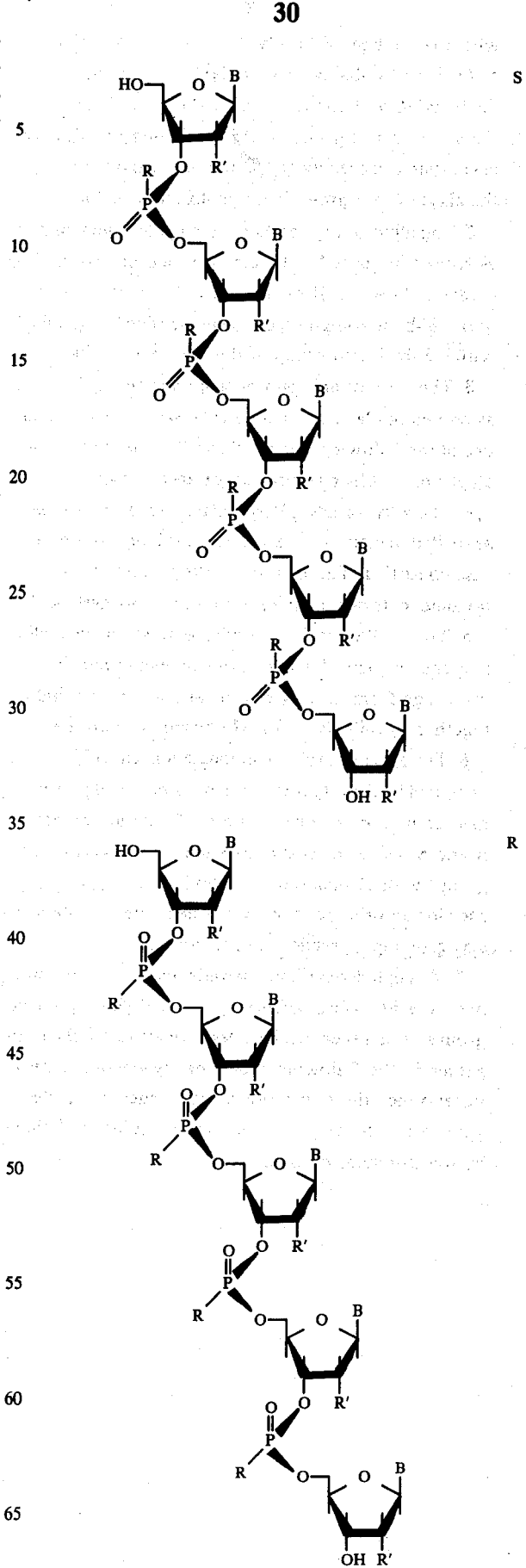

where B is a base; R' is a hydrogen, hydroxyl, O-alkyl or O-aryl or O-halogen; R is alkyl or aryl; and where the S and R configurations define the spatial location of the alkyl or aryl group, with R denoting the alkyl or aryl group in a pseudoequitorial position and S denoting the alkyl or aryl group in a pseudoaxial position.

2. The alkyl or aryl phosphonate nucleic acid analog as recited in claim 1, wherein each said nucleoside includes a 3'-hydroxyl group and a 5'-hydroxyl group, with a 3'-hydroxyl group of one nucleoside being linked with a 5'-hydroxyl group of the other nucleoside.

3. The alkyl or aryl phosphonate nucleic acid analog as recited in claim 1, wherein each said nucleoside has one of the following sugars: ribose, 2'-deoxyribose, 2'-O alkyl ribose, 2'halogenoribose, or aryl ribose.

4. The alkyl or aryl phosphonate nucleic acid analog as recited in claim 1, wherein each said nucleoside has a base consisting of at least one of the following: adenine, thymine, cytosine, guanine, uracil or hypoxanthine.

5. The alkyl or aryl phosphonate nucleic acid analog as recited in claim 1, wherein the number of nucleosides can range from at least five to at least twenty linked together by said alkyl or aryl phosphonate groups.

6. The alkyl or aryl phosphonate nucleic acid analog as recited in claim 1, wherein said alkyl or aryl phosphonate group consists of R and S configurations, wherein R and S define the spatial location of the alkyl or aryl group, with R denoting the alkyl or aryl group in a pseudoequitorial position and S denoting the alkyl or aryl group in a pseudoaxial position.

7. A heptadeoxyribonucleoside methylphosphonate nucleic acid analog comprising six methylphosphonate groups, and seven nucleosides, covalently linked together in the following order: deoxyadenosine, deoxyquanosine, deoxyguanosine, deoxyadenosine, deoxyguanosine, deoxyguanosine, and thymidine, as defined by the structural formula:

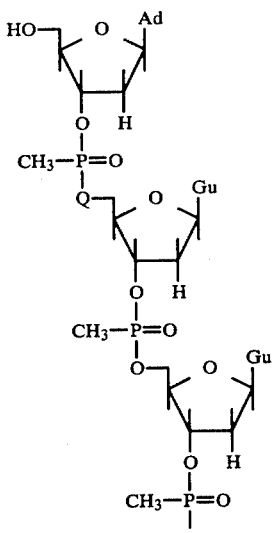
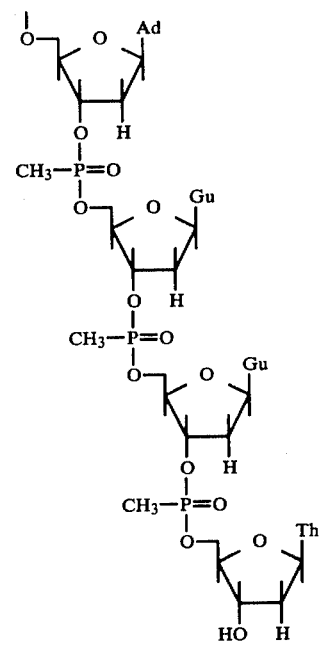

where Ad is adenine, Gu is guanine, and Th is thymine.

* * * * *